(12) United States Patent
Johns et al.

(10) Patent No.: US 8,973,736 B2
(45) Date of Patent: Mar. 10, 2015

(54) MAGNETIC DAMPING FOR SPECIMEN TRANSPORT SYSTEM

(71) Applicant: Beckman Coulter, Inc., Brea, CA (US)

(72) Inventors: Charles W. Johns, Brownsburg, IN (US); Samuel H. Rizzotte, Fishers, IN (US)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 13/670,884

(22) Filed: Nov. 7, 2012

(65) Prior Publication Data

US 2013/0126302 A1     May 23, 2013

Related U.S. Application Data

(60) Provisional application No. 61/556,667, filed on Nov. 7, 2011, provisional application No. 61/616,994, filed on Mar. 28, 2012, provisional application No. 61/680,066, filed on Aug. 6, 2012.

(51) Int. Cl.
*B65G 47/28*     (2006.01)
*G01N 35/04*     (2006.01)
(Continued)

(52) U.S. Cl.
CPC .............. *G01N 35/10* (2013.01); *B65G 47/28* (2013.01); *B01D 21/262* (2013.01); *B04B 7/08* (2013.01);
(Continued)

(58) Field of Classification Search
CPC ......... B65G 47/28; G01N 35/04; G01N 35/10

USPC ................... 198/439, 465.1, 465.2, 619, 679, 198/867.01, 867.11; 422/63, 65–67
See application file for complete search history.

(56) References Cited

U.S. PATENT DOCUMENTS 3,158,765 A    11/1964   Prolgreen
4,052,161 A    10/1977   Atwood et al.
(Continued)

FOREIGN PATENT DOCUMENTS

CA    1 282 692 A1    4/1991
CN    1127887 A      7/1996
(Continued)

OTHER PUBLICATIONS

Abe et al., "Quantitation of Hepatitis B Virus Genomic DNA by Real-Time Detection PCR," J. Clin. Microbiol., 1999, 37(9):2899-2903, American Society for Microbiology, Washington D.C., USA.
(Continued)

*Primary Examiner* — Mark A Deuble
(74) *Attorney, Agent, or Firm* — Kilpatrick Townsend & Stockton LLP

(57) ABSTRACT

A specimen transport system with magnetic damping and method for transporting specimens with magnetic damping are disclosed. A conveyance device transports sample carriers configured to carry specimen containers. One or more of the sample carriers include magnets. The system may also include a diverting arm having a magnet. When a first sample carrier is transported toward a second sample carrier, a first sample carrier magnet coupled to the first sample carrier repels a second sample carrier magnet coupled to the second sample carrier. When a sample carrier is transported toward a diverting arm, a diverting arm magnet of the diverting arm repels a sample carrier magnet of the sample carrier.

19 Claims, 8 Drawing Sheets

(51) Int. Cl.
*G01N 35/10* (2006.01)
*B01D 21/26* (2006.01)
*B04B 7/08* (2006.01)
*B04B 15/00* (2006.01)
*B25J 11/00* (2006.01)
*B04B 9/14* (2006.01)
*G01N 35/00* (2006.01)
*G01B 11/02* (2006.01)
*G01B 11/08* (2006.01)
*G01B 11/10* (2006.01)
*G01M 1/14* (2006.01)
*G01N 21/27* (2006.01)
*B04B 7/02* (2006.01)
*B04B 11/04* (2006.01)
*B01L 3/00* (2006.01)

(52) U.S. Cl.
CPC ............... *B04B 15/00* (2013.01); *B25J 11/00* (2013.01); *B04B 9/146* (2013.01); *G01N 35/00732* (2013.01); *G01N 35/0099* (2013.01); *G01N 35/04* (2013.01); *B04B 2011/046* (2013.01); *G01N 2035/00495* (2013.01); *G01N 2035/0405* (2013.01); *G01N 2035/0462* (2013.01); *G01N 2035/0491* (2013.01); *G01N 2035/1025* (2013.01); *G01N 2035/1032* (2013.01); *G01B 11/02* (2013.01); *G01B 11/08* (2013.01); *G01B 11/10* (2013.01); *G01M 1/14* (2013.01); *G01N 21/27* (2013.01); *G01N 35/1009* (2013.01); *B01L 3/5021* (2013.01); *B04B 7/02* (2013.01)
USPC ........................... 198/439; 198/465.1; 422/63

(56) References Cited

U.S. PATENT DOCUMENTS

| | | |
|---|---|---|
| 4,101,070 A | 7/1978 | Hoare et al. |
| 4,119,381 A | 10/1978 | Muka et al. |
| 4,250,266 A | 2/1981 | Wade |
| 4,401,189 A | 8/1983 | Majewski |
| 4,486,539 A | 12/1984 | Ranki et al. |
| 4,501,495 A | 2/1985 | Faulkner et al. |
| 4,530,056 A | 7/1985 | MacKinnon et al. |
| 4,593,238 A | 6/1986 | Yamamoto |
| 4,593,239 A | 6/1986 | Yamamoto |
| 4,673,657 A | 6/1987 | Christian |
| 4,674,640 A | 6/1987 | Asa et al. |
| 4,676,952 A | 6/1987 | Edelmann et al. |
| 4,683,195 A | 7/1987 | Mullis et al. |
| 4,683,202 A | 7/1987 | Mullis |
| 4,751,177 A | 6/1988 | Stabinsky |
| 4,780,817 A | 10/1988 | Lofgren |
| 4,800,159 A | 1/1989 | Mullis et al. |
| 4,851,330 A | 7/1989 | Kohne |
| 4,865,986 A | 9/1989 | Coy et al. |
| 4,943,415 A | 7/1990 | Przybylowicz et al. |
| 4,947,094 A | 8/1990 | Dyer et al. |
| 4,950,613 A | 8/1990 | Arnold, Jr. et al. |
| 5,055,393 A | 10/1991 | Kwoh et al. |
| 5,055,408 A | 10/1991 | Higo et al. |
| 5,075,853 A | 12/1991 | Luke, Jr. |
| 5,118,191 A | 6/1992 | Hopkins |
| 5,147,529 A | 9/1992 | Lee et al. |
| 5,154,888 A | 10/1992 | Zander et al. |
| 5,158,895 A | 10/1992 | Ashihara et al. |
| 5,168,766 A | 12/1992 | Stoffel |
| 5,179,329 A | 1/1993 | Nishikawa et al. |
| 5,185,439 A | 2/1993 | Arnold, Jr. et al. |
| 5,186,827 A | 2/1993 | Liberti et al. |
| 5,190,136 A | 3/1993 | Grecksch et al. |
| 5,196,168 A | 3/1993 | Muszak et al. |
| 5,205,393 A | 4/1993 | Malow et al. |
| 5,229,297 A | 7/1993 | Schinpelsky et al. |
| 5,234,665 A | 8/1993 | Ohta et al. |
| 5,244,055 A | 9/1993 | Shimizu |
| 5,283,174 A | 2/1994 | Arnold et al. |
| 5,283,739 A | 2/1994 | Summerville et al. |
| 5,288,463 A | 2/1994 | Chemelli |
| 5,330,916 A | 7/1994 | Williams et al. |
| 5,350,564 A | 9/1994 | Mazza et al. |
| 5,351,801 A | 10/1994 | Markin et al. |
| 5,362,291 A | 11/1994 | Williamson, IV |
| 5,366,697 A * | 11/1994 | Tomasso et al. .............. 422/64 |
| 5,366,896 A | 11/1994 | Margrey et al. |
| 5,374,395 A | 12/1994 | Robinson et al. |
| 5,375,898 A | 12/1994 | Ohmori et al. |
| 5,380,487 A | 1/1995 | Choperena et al. |
| 5,388,682 A | 2/1995 | Dudley |
| 5,389,339 A | 2/1995 | Petschek et al. |
| 5,397,709 A | 3/1995 | Berndt |
| 5,399,491 A | 3/1995 | Kacian et al. |
| 5,403,711 A | 4/1995 | Walder et al. |
| 5,415,839 A | 5/1995 | Zaun et al. |
| 5,422,271 A | 6/1995 | Chen et al. |
| 5,427,930 A | 6/1995 | Birkenmeyer et al. |
| 5,437,361 A * | 8/1995 | Ohmori et al. ............. 198/465.1 |
| 5,437,990 A | 8/1995 | Burg et al. |
| 5,443,791 A | 8/1995 | Cathcart et al. |
| 5,447,687 A | 9/1995 | Lewis et al. |
| 5,449,602 A | 9/1995 | Royer et al. |
| 5,462,881 A | 10/1995 | Perlman |
| 5,466,574 A | 11/1995 | Liberti et al. |
| 5,480,784 A | 1/1996 | Kacian et al. |
| 5,482,834 A | 1/1996 | Gillespie |
| 5,504,345 A | 4/1996 | Bartunek et al. |
| 5,514,550 A | 5/1996 | Findlay et al. |
| 5,525,300 A | 6/1996 | Danssaert et al. |
| 5,527,673 A | 6/1996 | Reinhartz et al. |
| 5,536,649 A | 7/1996 | Fraiser et al. |
| 5,538,849 A | 7/1996 | Uematsu et al. |
| 5,554,516 A | 9/1996 | Kacian et al. |
| 5,563,037 A | 10/1996 | Sutherland et al. |
| 5,578,270 A | 11/1996 | Reichler et al. |
| 5,582,796 A | 12/1996 | Carey et al. |
| 5,585,242 A | 12/1996 | Bourma et al. |
| 5,585,481 A | 12/1996 | Arnold, Jr. et al. |
| 5,587,128 A | 12/1996 | Wilding et al. |
| 5,589,333 A | 12/1996 | Bagasra et al. |
| 5,602,042 A | 2/1997 | Farber |
| 5,604,130 A | 2/1997 | Warner et al. |
| 5,612,200 A | 3/1997 | Dattagupta et al. |
| 5,612,525 A | 3/1997 | Apter et al. |
| 5,623,415 A | 4/1997 | O'Bryan et al. |
| 5,628,962 A | 5/1997 | Kanbara et al. |
| 5,637,275 A | 6/1997 | Carey et al. |
| 5,639,599 A | 6/1997 | Ryder et al. |
| 5,639,604 A | 6/1997 | Arnold et al. |
| 5,641,658 A | 6/1997 | Adams et al. |
| 5,652,489 A | 7/1997 | Kawakami |
| 5,653,940 A | 8/1997 | Carey et al. |
| 5,656,493 A | 8/1997 | Mullis et al. |
| 5,665,554 A | 9/1997 | Reeve et al. |
| 5,679,553 A | 10/1997 | Van Gemen et al. |
| 5,686,272 A | 11/1997 | Marshall et al. |
| 5,702,950 A | 12/1997 | Tajima |
| 5,705,062 A | 1/1998 | Knobel |
| 5,714,380 A | 2/1998 | Neri et al. |
| 5,720,377 A * | 2/1998 | Lapeus et al. ............. 198/346.1 |
| 5,720,923 A | 2/1998 | Haff et al. |
| 5,723,591 A | 3/1998 | Livak et al. |
| 5,730,938 A | 3/1998 | Carbonari et al. |
| 5,735,587 A | 4/1998 | Malin et al. |
| 5,741,708 A | 4/1998 | Carey et al. |
| 5,746,978 A | 5/1998 | Bienhaus et al. |
| 5,750,338 A | 5/1998 | Collins et al. |
| 5,773,268 A | 6/1998 | Korenberg et al. |
| 5,779,981 A | 7/1998 | Danssaert et al. |
| 5,786,182 A | 7/1998 | Catanzariti et al. |
| 5,795,547 A | 8/1998 | Moser et al. |
| 5,798,263 A | 8/1998 | Wood et al. |
| 5,814,008 A | 9/1998 | Chen et al. |

(56) References Cited

U.S. PATENT DOCUMENTS

| | | | |
|---|---|---|---|
| 5,814,276 A | 9/1998 | Riggs | |
| 5,814,961 A | 9/1998 | Imahashi | |
| 5,827,653 A | 10/1998 | Sammes et al. | |
| 5,846,489 A | 12/1998 | Bienhaus et al. | |
| 5,846,491 A | 12/1998 | Choperena et al. | |
| 5,846,726 A | 12/1998 | Nadeau et al. | |
| 5,857,955 A | 1/1999 | Phillips et al. | |
| 5,866,336 A | 2/1999 | Nazarenko et al. | |
| 5,881,781 A | 3/1999 | Bishop | |
| 5,882,903 A | 3/1999 | Andrevski et al. | |
| 5,895,631 A | 4/1999 | Tajima et al. | |
| 5,897,090 A | 4/1999 | Smith et al. | |
| 5,897,783 A | 4/1999 | Howe et al. | |
| 5,914,230 A | 6/1999 | Liu et al. | |
| 5,919,622 A | 7/1999 | Macho et al. | |
| 5,922,591 A | 7/1999 | Anderson et al. | |
| 5,925,517 A | 7/1999 | Tyagi et al. | |
| 5,928,907 A | 7/1999 | Woudenberg | |
| 5,948,673 A | 9/1999 | Cottingham et al. | |
| 5,966,309 A | 10/1999 | O'Bryan et al. | |
| 5,994,056 A | 11/1999 | Higuchi et al. | |
| 6,011,508 A | 1/2000 | Perreault et al. | |
| 6,033,574 A | 3/2000 | Siddiqi | |
| 6,033,880 A | 3/2000 | Haff et al. | |
| 6,043,880 A | 3/2000 | Andrews et al. | |
| 6,049,745 A | 4/2000 | Douglas et al. | |
| 6,056,106 A | 5/2000 | van Dyke, Jr. et al. | |
| 6,060,022 A | 5/2000 | Pang et al. | |
| 6,063,340 A | 5/2000 | Lewis et al. | |
| 6,068,978 A | 5/2000 | Zaun et al. | |
| 6,071,395 A | 6/2000 | Lange | |
| 6,100,079 A | 8/2000 | Tajima | |
| 6,110,676 A | 8/2000 | Coull et al. | |
| 6,110,678 A | 8/2000 | Weisburg et al. | |
| 6,117,398 A | 9/2000 | Bienhaus et al. | |
| 6,129,428 A | 10/2000 | Helwig et al. | |
| 6,150,097 A | 11/2000 | Tyagi et al. | |
| 6,165,778 A | 12/2000 | Kedar | |
| 6,171,780 B1 | 1/2001 | Pham et al. | |
| 6,212,448 B1 | 4/2001 | Xydis | |
| 6,277,332 B1 | 8/2001 | Sucholeiki | |
| 6,300,068 B1 | 10/2001 | Burg et al. | |
| 6,300,138 B1 | 10/2001 | Gleason et al. | |
| 6,306,658 B1 | 10/2001 | Turner et al. | |
| 6,333,008 B1 | 12/2001 | Leistner et al. | |
| 6,335,166 B1 | 1/2002 | Ammann et al. | |
| 6,353,774 B1 | 3/2002 | Goldenberg et al. | |
| 6,368,872 B1 | 4/2002 | Juranas | |
| 6,370,452 B1 | 4/2002 | Pfister | |
| 6,374,989 B1 | 4/2002 | van Dyke, Jr. et al. | |
| 6,377,888 B1 | 4/2002 | Olch | |
| 6,429,016 B1 | 8/2002 | McNeil | |
| 6,436,349 B1 | 8/2002 | Carey et al. | |
| 6,444,171 B1 | 9/2002 | Sakazume et al. | |
| RE37,891 E | 10/2002 | Collins et al. | |
| 6,458,324 B1 | 10/2002 | Schinzel | |
| 6,520,313 B1 | 2/2003 | Kaarakainen et al. | |
| 6,548,026 B1 | 4/2003 | Dales et al. | |
| 6,571,934 B1 * | 6/2003 | Thompson et al. | 198/619 |
| 6,586,234 B1 | 7/2003 | Burg et al. | |
| 6,586,255 B1 | 7/2003 | Hubert et al. | |
| 6,597,450 B1 | 7/2003 | Andrews et al. | |
| 6,599,476 B1 | 7/2003 | Watson et al. | |
| 6,605,213 B1 | 8/2003 | Ammann et al. | |
| 6,629,028 B2 | 9/2003 | Paromtchik et al. | |
| 6,633,785 B1 | 10/2003 | Kasahara et al. | |
| 6,692,708 B2 | 2/2004 | Chandler, Jr. | |
| 6,764,649 B2 | 7/2004 | Ammann | |
| 6,770,883 B2 | 8/2004 | McNeal et al. | |
| 6,818,183 B2 | 11/2004 | Hajduk et al. | |
| 6,890,742 B2 | 5/2005 | Ammann et al. | |
| 6,919,058 B2 | 7/2005 | Andersson et al. | |
| 6,919,175 B1 | 7/2005 | Bienhaus et al. | |
| 6,941,200 B2 | 9/2005 | Sonoyama et al. | |
| 6,993,176 B2 | 1/2006 | Yamagishi et al. | |
| 6,999,847 B2 | 2/2006 | Barry et al. | |
| 7,028,831 B2 | 4/2006 | Veiner | |
| 7,033,820 B2 | 4/2006 | Ammann et al. | |
| 7,045,358 B2 | 5/2006 | Chandler, Jr. | |
| 7,071,006 B2 | 7/2006 | Tajima et al. | |
| 7,078,698 B2 | 7/2006 | Itoh | |
| 7,118,892 B2 | 10/2006 | Ammann et al. | |
| 7,135,145 B2 | 11/2006 | Ammann et al. | |
| 7,174,836 B2 | 2/2007 | Marino et al. | |
| 7,264,111 B2 * | 9/2007 | Veiner | 198/619 |
| 7,267,795 B2 | 9/2007 | Ammann et al. | |
| 7,269,480 B2 | 9/2007 | Hashimoto et al. | |
| 7,273,749 B1 | 9/2007 | Wittwer et al. | |
| 7,288,229 B2 | 10/2007 | Turner et al. | |
| 7,362,258 B2 | 4/2008 | Kawabe et al. | |
| 7,419,830 B2 | 9/2008 | Canos et al. | |
| 7,463,948 B2 | 12/2008 | Orita | |
| 7,473,897 B2 | 1/2009 | Braendle et al. | |
| 7,482,143 B2 | 1/2009 | Ammann et al. | |
| 7,499,581 B2 | 3/2009 | Tribble et al. | |
| 7,524,652 B2 | 4/2009 | Ammann et al. | |
| 7,560,255 B2 | 7/2009 | Ammann et al. | |
| 7,560,256 B2 | 7/2009 | Ammann et al. | |
| 7,633,615 B2 * | 12/2009 | Emilsson | 356/244 |
| 7,688,448 B2 | 3/2010 | Bamberg et al. | |
| 7,771,659 B2 | 8/2010 | Ziegler | |
| 8,074,578 B2 | 12/2011 | Thornton | |
| 8,192,992 B2 | 6/2012 | Ammann et al. | |
| 2002/0025064 A1 | 2/2002 | Itoh | |
| 2002/0028489 A1 | 3/2002 | Ammann et al. | |
| 2002/0031768 A1 | 3/2002 | McMillan et al. | |
| 2002/0077239 A1 | 6/2002 | Evans, III et al. | |
| 2002/0086417 A1 | 7/2002 | Chen | |
| 2002/0098117 A1 | 7/2002 | Ammann et al. | |
| 2002/0123156 A1 | 9/2002 | Tajima | |
| 2002/0137194 A1 | 9/2002 | Ammann et al. | |
| 2002/0137197 A1 | 9/2002 | Ammann et al. | |
| 2002/0146347 A1 | 10/2002 | McNeil | |
| 2002/0147515 A1 | 10/2002 | Fava et al. | |
| 2003/0026736 A1 | 2/2003 | Hajduk et al. | |
| 2003/0027206 A1 | 2/2003 | Ammann et al. | |
| 2003/0054542 A1 | 3/2003 | Burns et al. | |
| 2003/0129614 A1 | 7/2003 | Parameswaran et al. | |
| 2003/0190755 A1 | 10/2003 | Turner et al. | |
| 2003/0213313 A1 | 11/2003 | Katagi | |
| 2003/0223916 A1 | 12/2003 | Testrut et al. | |
| 2004/0029260 A1 | 2/2004 | Hansen et al. | |
| 2004/0076983 A1 | 4/2004 | Karlsen | |
| 2004/0087426 A1 | 5/2004 | Lattanzi | |
| 2004/0115796 A1 | 6/2004 | Burns | |
| 2004/0158355 A1 | 8/2004 | Holmqvist et al. | |
| 2004/0184959 A1 | 9/2004 | Itoh | |
| 2004/0206419 A1 | 10/2004 | Ganz et al. | |
| 2004/0213651 A1 | 10/2004 | Malin | |
| 2005/0130198 A1 | 6/2005 | Ammann et al. | |
| 2005/0158212 A1 | 7/2005 | Yavilevich | |
| 2005/0163354 A1 | 7/2005 | Ziegler | |
| 2005/0207937 A1 | 9/2005 | Itoh | |
| 2005/0220670 A1 | 10/2005 | Palmieri et al. | |
| 2005/0233370 A1 | 10/2005 | Ammann et al. | |
| 2005/0239127 A1 | 10/2005 | Ammann et al. | |
| 2005/0266489 A1 | 12/2005 | Ammann et al. | |
| 2005/0271555 A1 | 12/2005 | Itoh | |
| 2006/0003373 A1 | 1/2006 | Ammann et al. | |
| 2006/0014295 A1 | 1/2006 | Ziegler | |
| 2006/0020370 A1 | 1/2006 | Abramson | |
| 2006/0148063 A1 | 7/2006 | Fauzi et al. | |
| 2006/0228268 A1 | 10/2006 | Heimberg et al. | |
| 2007/0044676 A1 | 3/2007 | Clark et al. | |
| 2007/0059209 A1 | 3/2007 | Pang et al. | |
| 2007/0100498 A1 | 5/2007 | Matsumoto et al. | |
| 2007/0110634 A1 | 5/2007 | Heimberg et al. | |
| 2007/0134131 A1 | 6/2007 | Watson et al. | |
| 2007/0179690 A1 | 8/2007 | Stewart | |
| 2007/0184548 A1 | 8/2007 | Tan et al. | |
| 2007/0193859 A1 | 8/2007 | Kyuyoku et al. | |
| 2007/0196237 A1 | 8/2007 | Neuzil et al. | |
| 2007/0208440 A1 | 9/2007 | Bliss et al. | |
| 2007/0225901 A1 | 9/2007 | Yamaguchi | |

(56) References Cited

U.S. PATENT DOCUMENTS

| | | |
|---|---|---|
| 2007/0225906 A1 | 9/2007 | Ikeda |
| 2008/0014181 A1 | 1/2008 | Ariff et al. |
| 2008/0015470 A1 | 1/2008 | Sarstedt |
| 2008/0056958 A1 | 3/2008 | Vijay et al. |
| 2008/0069730 A1 | 3/2008 | Itoh |
| 2008/0138249 A1 | 6/2008 | Itoh |
| 2008/0167817 A1 | 7/2008 | Hessler et al. |
| 2008/0241837 A1 | 10/2008 | Ammann et al. |
| 2008/0255683 A1 | 10/2008 | Takahashi et al. |
| 2008/0268528 A1 | 10/2008 | Ammann et al. |
| 2008/0274511 A1 | 11/2008 | Tan et al. |
| 2008/0297769 A1 | 12/2008 | Bamberg et al. |
| 2009/0029352 A1 | 1/2009 | Ammann et al. |
| 2009/0029871 A1 | 1/2009 | Ammann et al. |
| 2009/0029877 A1 | 1/2009 | Ammann et al. |
| 2009/0030551 A1 | 1/2009 | Hein et al. |
| 2009/0035185 A1 | 2/2009 | Tsujimura et al. |
| 2009/0042281 A1 | 2/2009 | Chang et al. |
| 2009/0047179 A1 | 2/2009 | Ping et al. |
| 2009/0117620 A1 | 5/2009 | Fritchie et al. |
| 2009/0318276 A1 | 12/2009 | Miler |
| 2009/0324032 A1 | 12/2009 | Chen |
| 2010/0018330 A1 | 1/2010 | Marty et al. |
| 2010/0115887 A1 | 5/2010 | Schroeder et al. |
| 2010/0129789 A1 | 5/2010 | Self et al. |
| 2010/0141756 A1 | 6/2010 | Grote et al. |
| 2010/0261595 A1 | 10/2010 | Schaefer et al. |
| 2010/0291619 A1 | 11/2010 | Robinson et al. |
| 2011/0065193 A1 | 3/2011 | Kitagawa et al. |
| 2011/0226584 A1 | 9/2011 | Ek |
| 2012/0129673 A1 | 5/2012 | Fukugaki et al. |
| 2013/0123089 A1 | 5/2013 | Johns et al. |
| 2013/0125675 A1 | 5/2013 | Muller et al. |
| 2013/0128035 A1 | 5/2013 | Johns et al. |
| 2013/0129166 A1 | 5/2013 | Muller et al. |

FOREIGN PATENT DOCUMENTS

| | | |
|---|---|---|
| CN | 1164894 A | 11/1997 |
| CN | 1212019 A | 3/1999 |
| CN | 1212021 A | 3/1999 |
| CN | 1245218 A | 2/2000 |
| CN | 1281462 A | 1/2001 |
| CN | 1974781 A | 6/2007 |
| DE | 35 10 797 C2 | 1/1998 |
| DE | 696 33 532 T2 | 2/2006 |
| EP | 0 324 616 A2 | 7/1989 |
| EP | 0 328 829 A2 | 8/1989 |
| EP | 0 410 645 A2 | 1/1991 |
| EP | 0 479 448 A2 | 4/1992 |
| EP | 0 502 589 A2 | 9/1992 |
| EP | 0 502 638 A2 | 9/1992 |
| EP | 0 542 422 A1 | 5/1993 |
| EP | 0 574 267 A2 | 12/1993 |
| EP | 0 574 267 A3 | 12/1993 |
| EP | 0 622 457 A1 | 2/1994 |
| EP | 0 600 130 A2 | 6/1994 |
| EP | 0 687 501 B1 | 12/1995 |
| EP | 0 656 864 B1 | 3/1996 |
| EP | 0 727 665 A2 | 8/1996 |
| EP | 0 763 739 A1 | 3/1997 |
| EP | 0 819 941 A2 | 1/1998 |
| EP | 0 875 584 A2 | 4/1998 |
| EP | 0 843 176 A1 | 5/1998 |
| EP | 0 680 883 B1 | 12/1998 |
| EP | 0 889 328 A | 7/1999 |
| EP | 0 953 838 A1 | 11/1999 |
| EP | 0 640 828 B1 | 5/2000 |
| EP | 1 069 942 B1 | 1/2001 |
| EP | 1 075 328 B1 | 2/2001 |
| EP | 0 875 584 A3 | 5/2001 |
| EP | 0 752 971 B1 | 6/2001 |
| EP | 1 205 756 A2 | 5/2002 |
| EP | 1 248 170 B1 | 10/2002 |
| EP | 1 273 919 A1 | 1/2003 |
| EP | 0 687 502 B1 | 3/2003 |
| EP | 1 288 758 B1 | 3/2003 |
| EP | 1 326 077 B1 | 9/2004 |
| EP | 1 557 961 A1 | 7/2005 |
| EP | 1 712 971 A2 | 10/2006 |
| EP | 1 712 971 A3 | 10/2006 |
| EP | 1 398 729 B1 | 10/2007 |
| EP | 1 024 355 B1 | 3/2008 |
| EP | 0 885 958 B1 | 6/2008 |
| EP | 1 138 784 B1 | 10/2008 |
| EP | 1 623 764 B1 | 2/2009 |
| EP | 1 614 470 B1 | 3/2009 |
| EP | 1 721 671 B1 | 10/2009 |
| EP | 1 731 222 B1 | 3/2010 |
| EP | 2 295 144 A | 3/2011 |
| EP | 2 316 570 A2 | 5/2011 |
| EP | 2 316 571 A2 | 5/2011 |
| EP | 2 316 572 A2 | 5/2011 |
| EP | 2 148 205 B1 | 1/2013 |
| GB | 2 101 514 A | 1/1983 |
| GB | 2 203 243 A | 10/1988 |
| JP | 62-148858 A | 7/1987 |
| JP | 01-211500 A1 | 8/1989 |
| JP | 02-025754 A2 | 1/1990 |
| JP | 05-184397 A | 7/1993 |
| JP | 05-219933 A | 8/1993 |
| JP | 05-281239 A | 10/1993 |
| JP | 06-011512 A | 1/1994 |
| JP | 06-197797 A | 7/1994 |
| JP | 06-327476 A | 11/1994 |
| JP | 07-049346 A | 2/1995 |
| JP | 07-75544 A | 3/1995 |
| JP | 07-191042 A | 7/1995 |
| JP | 07-213586 A | 8/1995 |
| JP | 07-107999 B2 | 11/1995 |
| JP | 07-301637 A | 11/1995 |
| JP | 07-333230 A | 12/1995 |
| JP | 08-9957 A | 1/1996 |
| JP | 08-62224 A | 3/1996 |
| JP | 08-211071 A | 8/1996 |
| JP | 08-285857 A | 11/1996 |
| JP | 08-286749 A | 11/1996 |
| JP | 08-320274 A | 12/1996 |
| JP | 09-021805 A | 1/1997 |
| JP | 09-080056 A | 3/1997 |
| JP | 09-089902 A | 4/1997 |
| JP | 09-89907 A | 4/1997 |
| JP | 09-121899 A | 5/1997 |
| JP | 09-329602 A | 12/1997 |
| JP | 10-062426 A | 3/1998 |
| JP | 11-503315 A | 3/1999 |
| JP | 2000-500331 A | 1/2000 |
| JP | 3007571 B2 | 2/2000 |
| JP | 2001-503730 A | 3/2001 |
| JP | 2002-296286 A | 10/2002 |
| JP | 2006-317330 A | 11/2006 |
| JP | 2007-249632 A | 9/2007 |
| JP | 2008-032652 A2 | 2/2008 |
| JP | 4511034 A | 5/2010 |
| JP | 4662580 A | 3/2011 |
| WO | 88/01302 A1 | 2/1988 |
| WO | 89/02476 A1 | 3/1989 |
| WO | 90/06042 A2 | 6/1990 |
| WO | 90/08840 A1 | 8/1990 |
| WO | 91/15768 A1 | 10/1991 |
| WO | 91/16675 A1 | 10/1991 |
| WO | 93/07292 A1 | 4/1993 |
| WO | 93/25912 A2 | 12/1993 |
| WO | 93/25912 A3 | 12/1993 |
| WO | 93/25913 A1 | 12/1993 |
| WO | 95/08774 A2 | 3/1995 |
| WO | 95/11454 A1 | 4/1995 |
| WO | 95/21382 A2 | 8/1995 |
| WO | 95/30139 A1 | 11/1995 |
| WO | 95/35390 A1 | 12/1995 |
| WO | 96/29602 A1 | 9/1996 |
| WO | 96/31781 A1 | 10/1996 |
| WO | 96/40990 A1 | 12/1996 |

(56) References Cited

FOREIGN PATENT DOCUMENTS

| | | |
|---|---|---|
| WO | 97/03348 A1 | 1/1997 |
| WO | 97/05492 A1 | 2/1997 |
| WO | 97/16561 A1 | 5/1997 |
| WO | 97/22882 A1 | 6/1997 |
| WO | 97/31105 A1 | 8/1997 |
| WO | 97/34908 A1 | 9/1997 |
| WO | 97/46707 A2 | 12/1997 |
| WO | 98/18008 A1 | 4/1998 |
| WO | 99/25476 A2 | 5/1999 |
| WO | 99/28724 A1 | 6/1999 |
| WO | 99/57561 A2 | 11/1999 |
| WO | 88/10315 A1 | 12/1999 |
| WO | 00/08472 A2 | 2/2000 |
| WO | 00/08472 A3 | 2/2000 |
| WO | 00/15481 A1 | 3/2000 |
| WO | 00/38046 A1 | 6/2000 |
| WO | 00/67547 A2 | 11/2000 |
| WO | 01/44510 A2 | 6/2001 |
| WO | 03/046412 A1 | 6/2003 |
| WO | 03/097808 A2 | 11/2003 |
| WO | 2004/013640 A1 | 2/2004 |
| WO | 2006/021052 A1 | 3/2006 |
| WO | 2006/068470 A1 | 6/2006 |
| WO | 2007/094744 A1 | 8/2007 |
| WO | 2008/030914 A2 | 3/2008 |
| WO | 2008/043393 A1 | 4/2008 |
| WO | 2008/057375 A2 | 5/2008 |
| WO | 2008/067847 A1 | 6/2008 |
| WO | 2009/068555 A1 | 6/2009 |
| WO | 2009/097263 A1 | 8/2009 |
| WO | 2009/150632 A2 | 12/2009 |
| WO | 2009/150632 A3 | 12/2009 |
| WO | 2010/017528 A2 | 2/2010 |
| WO | 2010/080340 A1 | 7/2010 |
| WO | 2010/081606 A1 | 7/2010 |
| WO | 2011/013701 A2 | 2/2011 |
| WO | 2011/028166 A1 | 3/2011 |
| WO | 2012/090795 A1 | 7/2012 |
| WO | 2012/158541 A1 | 11/2012 |

OTHER PUBLICATIONS

ABI Prism® 373 DNA Sequencer With XL Upgrade—User's Manual, Mar. 2001, TOC-iii-TOC-v & 6-11-6-16, Applied Biosystems, USA.

Abravaya, "Strategies to Avoid Amplicon Contamination," in Nucleic Acid Amplification Technologies: Application to Disease Diagnosis, 1997, pp. 125-133, Eaton Pub. Co., Natick, USA.

Akane, "Identification of the heme compound copurified with deoxyribonucleic acid (DNA) from bloodstains, a major inhibitor of polymerase chain reaction (PCR) amplification", J. Forensic Sci., 1994, 39:362-72, Blackwell Pub., USA.

Akduman et al., "Evaluation of a Strand Displacement Amplification Assay (BD ProbeTec-SDA) for Detection of Neisseria gonorrhoeae in Urine Specimens," J. Clin. Microbiol., 2002, 40(1):281-282, American Society for Microbiology, Washington D.C., USA.

Analog Device; "±5 g to ±5 g, Low Noise, Low Power, Single/Dual Axis / MEMS® Accelerometers,"; http://hibp.ecse.rpi.edu/~connor.education/EISpecs/ADXL150_250_0.pdf;; Jan. 1, 1998; pp. 1-15.

Anderson et al., "Microfluidic Biochemical Analysis System," Transducers, International Conference on Solib-Slate Sensors and Actuators, Jun. 16-19, 1997, p. 477-480, IEEE Electron Devices Society, Piscataway, USA.

Armstrong et al., 1996, "Automated high throughput RT-PCR," Laboratory Robotics and Automation 8:311-315, VCH Publishers, USA.

Bailey et al., "Robotic Nucleic Acid Isolation Using a Magnetic Bead Resin and an Automated Liquid Handler for Biological Agent Simulants,", JALA, Dec. 2003, 8:113-120.

Bassam. "Nucleic Acid Sequence Detection Systems: Revolutionary Automation for Monitoring and Reporting PCR Products" Australasian Biotechnology, 1996, 6:285-294, Australian Biotechnology Association, Australia.

Belgrader et al., "Automated DNA Purification and Amplification from Blood-Stained Cards Using a Robotic Workstation," Short Technical Reports, Biotechniques, 1995, 19(9):426-432, Informa Healthcare USA, Inc., UK.

Belgrader et al., "Automated Polymerase Chain Reaction Product Sample Preparation for Capillary Electrophoresis Analysis," J. Chromatogr. B Biomed. Appl., 1996, 683:109-114, Elsevier Science, Amsterdam, Netherlands.

Belgrader et al., "Automated Sample Processing Using Robotics for Genetic Typing of Short Tandem Repeat Polymorphisms by Capillary Electrophoresis," Laboratory Robotics and Automation, 1997, 9:3-7, Wiley & Sons Inc., USA.

Borst et al., "False-Positive Results and Contamination in Nucleic Acid Amplification Assays: Suggestions for a Prevent and Destroy Strategy," Eur. J. Clin. Microbiol. Infect Dis., 2004, 23:289-299, Springer-Verlag, Berlin, Germany.

Boyd et al., "Robotics and the changing face of the clinical laboratory," Clin. Chem., 1996, 42(12):1901-1910, Washington DC American Association for Clinical Chemistry, USA.

Brochure, "Introducing the Amplified Mycobacterium tuberculosis Direct (MTD) Test from Gen-Probe," Oct. 1996, Gen-Probe Incorporated, San Diego, USA, 2 pages.

Brochure, "The Future of Amplification Technology has Arrived," Oct. 1995, Gen-Probe Incorporated, San Diego, USA, 4 pages.

Buhlmann et al., "An Open Software Environment to Optimize the Productivity of Robotized Laboratories," J. Chromatogra. Sci., 1994, 32:243-248, Preston Technical Abstracts, Niles, USA.

Bush et al., "Detection of human immunodeficiency virus type 1 RNA in plasma samples from high-risk pediatric patients by using the self-sustained sequence replication reaction," J. Clin. Microbiol., 1992, 30(2):281-286, American Society for Microbiology, Washington D.C., USA.

Butler et al., "Forensic DNA typing by capillary electrophoresis using the ABI Prism 310 and 3100 genetic analyzers for STR analysis," Electrophoresis, 2004, 25:1397-1412, Wiley-VCH Verlag GmbH & Co. KGaA, Germany.

Caprari, G. et al.; "The autonomous Micro Robot "Alice": a platform for scientific and commercial applications"; Proceedings of the 1998 International Symposium on Micromechatronics and Human Science, Nagoya, Japan; Nov. 25-28, 1998; pp. 1-5.

Carlson et al., "Laboratory Detection of Chlamydia trachomatis, Neisseria gonorrhoeae, and Other Sexually-Transmitted Agents," 97th General Meeting of the American Society for Microbiology, C-308, May 4-8, 1997, Miami Beach, USA.

Carrino et al., "Nucleic Acid Amplification Methods," J. Micorbiol. Methods, 1995, 23:3-20.

Check, "Real-time PCR for the rest of us," CAP Today, Jun. 2006, College of American Pathologists, Skokie, IL, USA, 6 pages.

Chemistry Guide, "Automated DNA Sequencing," PE Applied Biosystems, 1998, pp. 1-4-1-6, The Perkin-Elmer Corporation.

Cimino et al., "Post-PCR sterilization: a method to control carryover contamination for the polymerase chain reaction," Nucleic Acids Res., 1991, 19(1):99-107, Oxford University Press, Oxford, United Kingdom.

Clewley, "Automation of the Polymerase Chain Reaction Part 2. Extraction—the Foundation for Success," Communicable Disease and Public Health, Jun. 1999, 2(2):147-148, Public Health Laboratory Service in association with the Scottish Centre for Infection and Environmental Health, London, United Kingdom.

Corkan et al., "Experiment Manager Software for an Automated Chemistry Workstation, Including a Scheduler for Parallel Experimentation," Chemometrics and Intelligent Laboratory Systems: Laboratory Information Management, 1992, 17:47-74, Elsevier Science Publishers, Amsterdam, Netherlands.

Corrected Request for Inter Partes Reexamination of U.S. Patent No. 7,482,143, filed on Sep. 14, 2012, 121 pages.

Crotchfelt et al., "Detection of Chlamydia trachomatis by the Gen-Probe Amplified Chlamydia trachomatis Assay (AMP CT) in Urine Specimens from Men and Women and Endocervical Specimens from Women," J. Clin. Microbiol., Feb. 1998, 36(2):391-394, American Society for Microbiology, Washington D.C., USA.

(56) References Cited

OTHER PUBLICATIONS

Davis et al., "Amplification of DNA Using the Polymerase Chain Reaction," in Basic Methods in Molecular Biology, 2nd ed., 1994, p. 121, Appleton & Lange, Norwalk, USA.

Diamandis, "Automation of molecular diagnostics," Clinical Chemistry, 1996, 42:7-8, American Association for Clinical Chemistry, USA.

DiDomenico et al., "Cobas Amplicor™ : fully automated RNA and DNA amplification and detection system for routine diagnostic PCR," Clin. Chem., 1996, 42(12):1915-1923, Washington Dc American Association for Clinical Chemistry, USA.

Dieffenbach et al., "Setting Up a PCR Laboratory," Genome Rsearch, PCR Methods and Applications, 1993, 3:s2-s7, Cold Spring Harbor Laboratory, Cold Spring Harbor, USA.

Dragon, "Handling Reagents in the PCR Laboratory," Genome Research, PCR Methods and Applications, 1993, 3:s8-s9, Cold Spring Harbor Laboratory, Cold Spring Harbor, USA.

Dynal®, Technical Handbook. Molecular Biology, First Edition. "Dynabeads® biomagnetic separation system," 1992, 4 pages, Dynal AS, Norway.

Erlich, "PCR Technology," in Encyclopedia of Molecular Biology and Molecular Medicine: Mass Spectrometry High Speed DNA Fragment Sizing to Plasma Lipoproteins, vol. 4, 1996, p. 337, VCH Verlagsgesellschaft mbH, Weinheim, Germany.

Espy et al., "Dependence of polymerase chain reaction product inactivation protocols on amplicon length and sequence composition," J. Clin. Microbiol., 1993, 31(9):2361-2365, American Society for Microbiology, Washington D.C., USA.

Farrell, Jr., "RT PCR" in RNA Method: A Laboratory Guide for Isolation and Characterization, 1998, 2nd ed., Chapter 15, pp. 296-307, Academic Press, San Diego, California, USA.

Feinberg, "A Technique for Radiolabeling DNA Restriction Endonuclease Fragments to High Specific Activity", Analytical Biochemistry, 1983, 132:6-13, Academic Press, USA.

Findlay et al., "Automated Closed-Vessel System for in Vitro Diagnostics Based on Polymerase Chain Reaction," Clin. Chem., 1993, 39(9):1927-1933, American Association for Clinical Chemistry, Washington, D.C., USA.

Fiore et al., "The Abbott IMx automated benchtop immunochemistry analyzer system," Clin. Chem., 1988, 34 (9):1726-32, American Association for Clinical Chemistry, Washington D.C., USA.

Flexlink®; "TX45E puck handling (mx. 250g),"; located at http://www.flexlink.com/en/offering/conveyor-systems/pallet-and-puck-handling/x45e.jsp; last visited on Jul. 20, 2013; 2 pages.

Friendenberg et al., "Developing a fully automated instrument for molecular diagnostic assays," IVD Technology, 2005, 11(6), 6 pages, A Canon Communications, Los Angeles, USA.

Furrows et al., "'Good laboratory practice' in diagnostic laboratories using nucleic acid amplification methods," Clin. Microbiol. Infect., 2001, 7(5):227-229, Blackwell Science, Oxford, United Kingdom.

Gelmini et al., "Quantitative polymerase chain reaction-based homogeneous assay with fluorogenic probes to measure c-erbB-2 oncogene amplification," Clin. Chem., 1997, 43(5):752-758, American Association for Clinical Chemistry, Washington D.C., USA.

Gerber et al., "Differential Transcriptional Regulation of the Two Vascular Endothelial Growth Factor Receptor Genes," J. Biol. Chem., 1997, 272(38):23659-23667, The American Society for Biochemistry and Molecular Biology, Baltimore, USA.

Gibson et al., "A homogenous method for genotyping with fluorescence polarization," Clin. Chem., 1997, 43(8):1336-1341, American Association for Clinical Chemistry, Washington D.C., USA.

Gibson et al., "A novel method for real time quantitative RT-PCR," Genome Methods, 1996, 6:995-1001, Cold Spring Harbor Laboratory Press, Cold Spring Harbor, USA.

Giesendorf et al., "Molecular beacons: a new approach for semiautomated mutation analysis," Clin. Chem., 1998, 44(3):482-486, American Association for Clinical Chemistry, Washington D.C., USA.

Gilgen et al., "Hydroxyquinoline overcomes PCR inhibition by UV-damaged mineral oil," Nucleic Acids Res., 1995, 23(19):4001-4002, Oxford University Press, Oxford, United Kingdom.

Ginocchio, "Life Beyond PCR: Alternative Target Amplification Technologies for the Diagnosis of Infectious Diseases, Part II," Clinical Microbiology Newsletter, 2004, 26(17):129-136, Elsevier Science, New York, USA.

Godfrey-Faussett, "Molecular Diagnosis of Tuberculosis: The Need for New Diagnostic Tools," Thorax, 1995, 50(7):709-711, British Medical Association, London, United Kingdom.

Greenstein, "Preparing and Using M13-Derived Vectors," Current Protocols in Molecular Biology, published 1990, §1.151 and 1.15.4, J. Wiley and Sons, USA.

Haas, "Clinical Instrumentation (General Chemistry and Immunoassay Analyzers)," Anal. Chem., 1993, 65(12):444R-449R, American Chemical Society, Washington D.C., USA.

Haglund et al., "Polymerase Chain Reaction," in Forensic Taphonomy: the Postmortem Fate of Human Remains, 1997, p. 114-115, CRC Press LLC, Boca Raton, USA.

Hartley et al., "Dealing with Contamination: Enzymatic Control of Carryover Contamination in PCR," Genome Research, PCR Methods and Applications, 1993, 3:s10-s14, Cold Spring Harbor Laboratory, Cold Spring Harbor, USA.

Hawker, "Laboratory Automation: Total and Subtotal," Clin. Lab. Med., 2007, 27:749-770, Elsevier Health Sciences Division, Philadelphia, USA.

Hawkes et al., "Asymptomatic carriage of *Haemophilus ducreyi* confirmed by the polymerase chain reaction," J. Genitourin. Med., 1995, 71:224-227.

Hawkins et al., "A Magnetic Attraction to High-Throughput Genomics," Science, 1997, 276:1887 & 1889 (p. 1888 omitted—advertisement only), Washington, DC: American Association for the Advancement of Science, USA.

Hedrum et al., "Immunomagnetic Recovery of *Chlamydia trachomatis* from Urine with Subsequent Colorimetric DNA Detection," PCR Methods Appl., 1992, 2:167-171, Cold Spring Harbor Laboratory Press, Cold Spring Harbor, USA.

Heid et al., "Real Time Quantitative PCR," Genome Research, 1996, 6:986-994, Cold Spring Harbor Laboratory Press, Cold Spring Harbor, USA.

Hellyer et al., "Letter to the Editor: Specificity of IS6110-Based Amplification Assays for *Mycobacterium tuberculosis* Complex," J. Clin. Microbiol., 1997, 35(3):799-801, American Society for Microbiology, Washington D.C., USA.

Herring et al., "ELISA Automation: A Biomek 1000 to Biomek 2000 Comparison of Clinical ELISAs", Application Information, 1995, Beckman Industries, Inc., USA.

Herrmann et al., "General Aspects of Sample Preparation," in Ancient DNA: Recovery and Analysis of Genetic Material from Paleontological, Archaeological, Museum, Medical, and Forensic Specimens, 1994, pp. 63-64, Springer-Verlag, New York City, USA.

Hicks et al., "Beckman/Sagian "Core" Molecular Biology System,", T-1845A, Beckman Instruments, Inc., 1997, 4 pages.

Higuchi et al., "Simultaneous Amplification and Detection of Specific DNA Sequences," Bio/Technology, 1992, 10:413-417, Nature Publishing Company, New York, USA.

Hildebrandt et al,, Development of an Automated Sample Preparation Method for HCV, J. Microbiol. Methods, 1997, 30:235-253, Abstract 17, 1 page, Elsevier Biomedical, Amsterdam, Netherlands.

Hill, "Gen-Probe Transcription-Mediated Amplification: System Principles," Jan. 1996, Gen-Probe Incorporated, San Diego, USA, 4 pages.

Hill, "How Full Automation of Molecular Diagnostic Testing Can Increase Accuracy, Lab Efficiency, Cost Savings," Issue Stories, Jul. 2004, 3 pages, Clinical Lab Products, Los Angeles, USA.

Hill, "Molecular diagnostic testing for infectious diseases using TMA technology," Expert Rev. Mol. Diagn., 2001, 1 (4):445-455, Future Drugs Ltd., London, United Kingdom.

Hill, "Molecular Diagnostic Tests for Sexually Transmitted Infections in Women," in Infectious Diseases in Obstetrics and Gynecology, 2008, 6th ed., pp. 612-623, Informa plc, St. Helier, Jersey.

(56) References Cited

OTHER PUBLICATIONS

Hill, "Molecular Diagnostics for Infectious Diseases," J. Clin. Ligand Assay, 1996, 19(1):43-52, Clinical Ligand Assay Society, Wayne, Michigan, USA.

Hoad et al., "Virus Genome Detection by the PCR," in Practical Molecular Virology: Viral Vectors for Gene Expression, 1991, pp. 75-76, Humana Press, Totowa, USA.

Holland et al., "Detection of specific polymerase chain reaction product by utilizing the 5'→ 3' exonuclease activity of *Thermus aquaticus* DNA polymerase," Biochemistry, 1991, 88:7276-7280, Proc. Natl. Acad. Sci. USA, Washington D.C., USA.

International Search Report and Written Opinion mailed on Feb. 15, 2013 for PCT Application No. PCT/US2012/063914, 9 pages.

International Search Report and Written Opinion mailed on Jun. 12, 2013 for PCT Patent Application No. PCT/US2012/063888, 18 pages.

International Search Report and Written Opinion mailed on Mar. 19, 2013 for PCT Application No. PCT/US2012/063929, 13 pages.

International Search Report and Written Opinion mailed on Dec. 7, 2012 for PCT Patent Application No. PCT/US2011/045107, 18 pages.

International Search Report and Written Opinion mailed on Oct. 4, 2013 for PCT Patent Application No. PCT/US2012/063931, 24 pages.

International Search Report and Written Opinion mailed on Sep. 30, 2013 for PCT Patent Application No. PCT/US2012/063930, 37 pages.

Invitation to Pay Additional Fees mailed on Mar. 1, 2013 for PCT Patent Application No. PCT/US2012/063918, 6 pages.

Invitation to Pay Additional Fees mailed on Mar. 19, 2013 for PCT Patent Application No. PCT/US2012/063930, 8 pages.

Invitation to Pay Additional Fees mailed on Mar. 25, 2013 for PCT Patent Application No. PCT/US2012/063931, 8 pages.

Invitation to Pay Additional Fees mailed on Mar. 6, 2013 for PCT Patent Application No. PCT/US2012/063888, 6 pages.

Invitrogen; Manual, "Dynabeads® DNA Direct™ Blood Cat. No. 631.02 "For the isolation of PCR-ready genomic DNA from blood" Rev. o. 006," Invitrogen, *Dynal® Invitrogen Bead Separations*, 2007.

Jaton et al., "Development of polymerase chain reaction assays for detection of *Listeria monocytogenes* in clinical cerebrospinal fluid samples," J. Clin. Microbiol., 1992, 30(8):1931-1936, American Society for Microbiology, Washington D.C., USA.

Jungkind et al., "Evaluation of Automated Cobas Amplicor PCR System for Detection of Several Infectious Agents and Its Impact on Laboratory Management," J. Clin. Microbiol., 1996, 34(11):2778-2783, American Society for Microbiology, Washington, D.C., USA.

Kalinina et al., "Nanoliter scale PCR with TagMan detection," Nucleic Acids Res., 1997, 25(10):1999-2004, Oxford University Press, Oxford, United Kingdom.

Kapperud et al., "Detection of Pathogenic *Yersinia enterocolitica* in Foods and Water by Immunomagnetic Separation, Nested Polymerase Chain Reactions, and Colorimetric Detection of Amplified DNA," Appl. Environ. Microbiol., 1993, 59(9):2938-2944, American Society for Microbiology, Washington, D.C., USA.

Kendrew et al., "Polymerase Chain Reaction," in The Encyclopedia of Molecular Biology, 1994, pp. 864-865, Blackwell Science Ltd., Cambridge, USA.

Khalil "Automation and Use of Robotics in Nucleic Acid Amplification Assays," in Nucleic Acid Amplification Technologies: Application to Disease Diagnosis, 1997, p. 151-164, Eaton Pub. Co., Natick, USA.

Kolk et al., "Development of Individual and Multiplex Assays for the Detection of HIV and HCV," 13th Annual Clinical Virology Symposium and Annual Meeting of the Pan American Society for Clinical Virology, M7, Apr. 27-30, 1997, Clearwater Beach, USA.

Kolmodin et al., "Basic Principles and Routine Practice," in PCR Cloning Protocols From Molecular Cloning to Genetic Engineering, 1997, pp. 3-5, Humana Press, Totowa, USA.

Kost, G. J., *Handbook of Clinical Automation, Robotics, and Optimization*; Chapters 1, 10, and 12-14; 1996 by John Wiley & Sons, Inc.; 189 pages total.

Kretz et al., "Cycle sequencing," PCR Methods and Applications, 1994, 3:S107-S112, Cold Spring Harbor Laboratory, Cold Spring Harbor Press, USA.

Krieg, "Quantification of RNA by Competitive RT PCR," in A Laboratory Guide to RNA, 1996, p. 210, Wiliey-Liss, New York City, USA.

Kwok et al., "Avoiding False Positive with PCR," Nature, 1989, 339:237-238, Nature Publishing Group, Basingstoke, USA.

Landry, "False-Positive Polymerase Chain Reaction Results in the Diagnosis of Herpes Simplex Encephalitis," J. Infect. Dis., 1995, 172(6):1641-1642, University of Chicago Press, Chicago, USA.

Lay et al., "Real-time fluorescence genotyping of factor V Leiden during rapid-cycle PCR," Clin. Chem., 1997, 43(12):2262-2267, American Association for Clinical Chemistry, Washington D.C., USA.

Lee et al., "Direct Identification of *Vibrio vulmificus* in Clinical Specimens by Nested PCR," J. Clin. Microbial., 1998, 36 (10):2887-2892, American Society for Microbiology, Washington D.C., USA.

Lee et al., "Nucleic Acid Amplification Technologies: Application to Disease Diagnosis," BioTechniques Books, 1997, pp. 1-286, Eaton Publishing, Massachusetts, USA.

Leone et al., "Molecular beacon probes combined with amplification by NASBA enable homogeneous, real-time detection of RNA," Nucleic Acids Res., 1998, 26(9): 2150-2155, Oxford University Press, Oxford, United Kingdom.

Lisby, "Application of Nucleic Acid Amplification in Clinical Microbiology," in Methods in Molecular Biology: PCR in Bioanalysis, 1998, pp. 1-29, Humana Press, Totowa, USA.

Livak et al., "Oligonucleotides with Fluorescent Dyes at Opposite Ends Provide a Quenched Probe System Useful for Detecting PCR Product and Nucleic Acid Hybridization," PCR Methods and Applications, 1995, 4:357-362, Cold Spring Harbor Laboratory Press, Cold Spring Harbor, New York, USA.

Lo et al., "Quantitative Analysis of Fetal DNA in Maternal Plasma ad Serum: Implications for Noninvasive Prenatal Diagnosis," 1998, Am. J. Hum. Genet., 62:768-775, American Society of Human Genetics, Baltimore, USA.

Lo, "Setting Up a PCR Laboratory," in Methods in Molecular Medicine: Clinical Applications of PCR, 1998, pp. 12-17, Humana Press, Totowa, USA.

Longo, "Use of uracil DNA glycosylase to control carry-over contamination in polymerase chain reactions" Gene, 1990, 93: 125-128, Elsevier/North-Holland, Amsterdam.

Mabilat et al., "Routine Identification of *Mycobacterium Tuberculosis* Complex Isolates by Automated Hybridization," J. Clin. Microbiol., 1994, 32(11):2702-2705, American Society for Microbiology, Washington, D.C., USA.

Magnemotion; "MagneMover™ LITE,"; located at http://www.magnemotion.com/industrial-automation/magmoverlite.cfm; last visited on Jul. 20, 2013; 3 pages.

Mangiapan, "Sequence capture-PCR improves detection of mycobacterial DNA in clinical specimens" J Clin Microbiol., 1996, 34: 1209-1215, American Society for Microbiology, USA.

Martin et al., "PCR and Its Modifications for the Detection of Infectious Disease," Nucleic Acid Amplification Technologies: Application to Disease Diagnosis, 1997, p. 79-100, Eaton Pub. Co., Massachusetts, USA.

McCreedy et al., "Laboratory Design and Work Flow," Diagnostic Molecular Microbiology Principles and Applications, 1993, p. 149-159, Mayo Foundation, Rochester, USA.

Meng et al., "Turbo PCR—An Integrated Robotic System for Continuously Setting Up and Running Multiple PCR Reactions," DOE Human Genome Program Contractor-Grantee Workshop IV, Nov. 13-17, 1994, Santa Fe, New Mexico, 1 page.

Mercier et al., "Direct PCR from whole blood, without DNA extraction," Nucleic Acids Res., 1990, 18(19):5908, Oxford University Press, Oxford, United Kingdom.

Merel et al., "Completely Automated Extraction of DNA from Whole Blood," Clin. Chem., 1996, 42(8):1285-1286, American Association for Clinical Chemistry, USA.

(56) References Cited

OTHER PUBLICATIONS

Merel et al., "Perspectives on Molecular Diagnostics Automation," JALA, 2005, 10:342-350, Association for Laboratory Automation, Charlottesville, USA.

Meyers, "PCR Technology," Molecular Biology and Biotechnology: A Comprehensive Desk Reference, 1995, pp. 642-646, VCH Publishers Inc., New York City, USA.

Mischiati et al., "Use of an Automated Laboratory Workstation for Isloation of Genomic DNA Suitable for PCR and Allele-Specific Hybridization," BioTechniques, 1993, 15(1):146-151, Eaton Pub. Co., Natick, USA.

Mondada, Francesco et al.; "The e-Puck, a Robot Designed for Education in Engineering", *Proceedings of the 9th Conference on Autonomous Robot Systems and Competitions*, Castelo Branco, Portugal; May 7, 2009; vol. 1; Issue 1; pp. 59-65.

Mullis, "Eine Nachtfahrt and die Polymerase-Kettenreaktion," Spektrum der Wissenschaft, 1950, pp. 60-67, Germany.

Muramatsu et al., "Molecular Cell Biology Dictionary," 1997, Tokyo Kagaku Dojin Publisher, Tokyo, Japan, English Translation, 10 pages.

Nace, "Automation in Molecular Diagnostics: A Pleasant Surprise," Advance for Medical Laboratory Professionals, 2006, 14(11):64, Merion Publications, King of Prussia, PA, USA.

Nazarenko et al., "A closed tube format for amplification and detection of DNA based on energy transfer," Nucleic Acids Res., 1997, 25(12):2516-2521, Oxford University Press, Oxford, United Kingdom.

Neumaier et al., "Fundamentals of Quality Assessment of Molecular Amplification Methods in Clinical Diagnostics," Clin. Chem., 1998, 44(1):12-26, American Society for Clinical Chemistry, Washington D.C., USA.

Newton et al., "Instrumentation, Reagents and Consumables," PCR, 1996, 2nd ed., Chpt. 2, pp. 9-28, Bios Scientific, UK.

Nickerson et al., "Automated DNA Diagnostics Using an ELISA-based Oligonucleotide Ligation Assay," Proc. Natl. Acad. Sci. USA, 1990, 87:8923-8927, National Academy of Sciences, Washington, D.C., USA.

Niederhauser et al., "Direct Detection of *Listeria monocytogenes* Using Paramagnetic Bead DNA Extraction and Enzymatic DNA Amplificaiton,", Molecular and Cellular Probes, 1994, 8:223-228.

Noordhoek et al., "Reliability of Nucleic Acid Amplification for Detection of *Mycobacterium Tuberculosis*: an International Collaborative Quality Control Study Among 30 Laboratories," J. Clin. Microbiol., 1996, 34(10):2522-2524, American Society for Microbiology, Washington D.C., USA.

Obata et al., "Development of a Novel Method for Operating Magnetic Particles, Magtration Technology, and Its Use for Automating Nucleic Acid Purification," J. Biosci. Bioeng., 2001, 91(5):500-503, Elsevier Science, Amsterdam, Netherlands.

Oehlenschlager et al., "Detection of HIV-1 RNA by nucleic acid sequence-based amplification combined with fluorescence correlation spectroscopy," Biochemistry, 1996, 93:12811-12816, Proc. Natl. Acad. Sci. USA, Washington D.C., USA.

Olive, "Q-Beta Replicase Assays for the Clinical Detection of Infectious Agents," in Nucleic Acid Amplification Technologies: Application to Disease Diagnosis, 1997, p. 110, Eaton Pub. Co., Natick, USA.

Olsvik et al., "Magnetic Separation Techniques in Diagnostic Microbiology," Clin. Microbiol. Rev., 1994, 7(1):43-54, American Society for Microbiology, Washington, D.C., USA.

Oste, "Polymerase Chain Reaction," Product Application Focus, BioTechniques, 1988, 6(2):162-167, Informa Healthcare USA, Inc., UK.

Package Insert, "Aptima® Assay for *Neisseria gonorrhoeae*," IN0148-01-REG, Rev. 1, Nov. 2004, Gen-Probe Incorporated, San Diego, USA, 20 pages.

Package Insert, "Aptima® HCV RNA Qualitative Assay," 500237 Rev. B, Jul. 2006, Gen-Probe Incorporated, San Diego, USA, 18 pages.

Package Insert, "Gen-Probe® Amplified *Mycobacterium tuberculosis* Direct Test," IN0006 Rev. A, Feb. 24, 1994, Gen-Probe Incorporated, San Diego, USA, 14 pages.

Package Insert, "Gen-Probe® Amplified™ *Chlamydia trachomatis* Assay," IN0012 Rev. A, Jan. 6, 1997, Gen-Probe Incorporated, San Diego, USA, 17 pages.

Package Insert, "Gen-Probe® Amplified™ *Chlamydia Trachomatis* Swab Specimen Preparation Kit," In0016 Rev. A, Jan. 6, 1997, Gen-Probe Incorporated, San Diego, USA, 3 pages.

Package Insert, "Gen-Probe® Amplified™ *Chlamydia trachomatis* Urine Specimen Preparation Kit," IN0017 Rev. A, Nov. 11, 1996, Gen-Probe Incorporated, San Diego, USA, 3 pages.

Package Insert, "Gen-Probe® Aptima® Combo 2 Assay," IN0037 Rev. A, Jun. 6, 2001, Gen-Probe Incorporated, San Diego, USA, 28 pages.

Package Insert, "Gen-Probe® Aptima Combo 2® Assay," 501011 Rev. A, Jan. 2007, Gen-Probe Incorporated, San Diego, USA, 44 pages.

Package Insert, "Gen-Probe® Aptima® Assay for *Chlamydia trachomatis*," IN0147-01, Rev. B, Apr. 2005, Gen-Probe Incorporated, San Diego, USA, 24 pages.

Package Insert, "Procleix® HIV-1/HCV Assay," IN0076-01-FDA, Rev. 3, Jun. 2004, Gen-Probe Incorporated, San Diego, USA, 28 pages.

Package Insert, "Procleix® HIV-1/HCV Assay," IN0076-02-FDA, Rev. 1, Jan. 2005, Gen-Probe Incorporated, San Diego, USA., 32 pages.

Package Insert, "Procleix® Ultrio™ Assay," IN0167EN, Rev. 1, Aug. 2004, Gen-Probe Incorporated, San Diego, USA, 44 pages.

Package Insert, "Procleix® WNV Assay," IN0155, Rev. 1, Apr. 2004, Gen-Probe Incorporated, San Diego, USA, 15 pages.

Paillard et al., "Direct nucleic acid diagnostic tests for bacterial infectious diseases: Streptococcal pharyngitis, pulmonary tuberculosis, vaginitis, chlamydial and gonococcal infections," MLO, Jan. 2004, pp. 10-15, Medical Laboratory Observer, NP Communications, LLC, Monroe Township, USA.

Panaccio et al., "PCR based diagnosis in the presence of 8% (v/v) blood," Nucleic Acids Res., 1991, 19(5):1151, Oxford University Press, Oxford, United Kingdom.

Patel et al., "Death from Inappropriate Therapy for Lyme Disease," Clin. Infect. Dis., 2000, 31:1107-1109, The University of Chicago Press, Chicago, USA.

Patterson et al., "Random and continuous-access immunoassays with chemiluminescent detection by Access automated analyzer," Clin. Chem., 1994, 40(11):2042-2045, American Association for Clinical Chemistry, Washington D.C., USA.

Pauwels et al., "Automated techniques in biotechnology," Current Opinion in Biotechnology, 1995, 6:111-117, Current Biology Ltd., London, United Kingdom.

Pawlotsky, "Measuring Hepatitis C Viremia in Clinical Samples: Can We Trust the Assays?" J. Hepatol., 1997, 26(1):1-4, Viral Hepatitis Foundation Bangladesh, Dhaka, Bangladesh.

Persing, "Diagnostic molecular microbiology. Current challenges and future directions," Diagn. Microbiol. Infect. Dis., 1993, 16(2):159-163, Elsevier Biomedical, New York, USA.

Petrik et al., "Human Hepatic Glyceraldehyde-3-phosphate dehydrogenase Binds to the poly(U) tract of the 3' Non-Coding Region of Hepatitis C Virus Genomic RNA," J. General Virology, 1999, 80:3109-3113.

Request for *Inter Partes* Reexamination of U.S. Patent No. 7,524,652, filed on Sep. 15, 2012, 134 pages.

Riggio et al., "Identification by PCR of *Helicobacter pylori* in subgingival plaque of adult periodontitis patients," J. Med. Microbiol., 1999, 48:317-322, The Pathological Society of Great Britain and Ireland.

Rosenblum et al., "New dye-labeled terminators for improved DNA sequencing patterns," Nucleic Acids Res., 1997, 25(22):4500-4504, Oxford University Press, UK.

Rudi et al., "Rapid, Universal Method to Isolate PCR-Ready DNA Using Magnetic Beads," BioTechniques, 1997, 22(3):506-511, Informa Healthcare USA, Inc., UK.

(56) References Cited

OTHER PUBLICATIONS

Rudi, et al., "Detection of Toxin-Producing Cyanobacteria by Use of Paramagnetic Beads for Cell Concentration and DNA Purification," 1998, Appl. Environ. Microbiol., 64(1):34-37, Am. Society of Microbiol., USA.
Schepetiuk et al., "Detection of *Chlamydia trachomatis* in Urine Samples by Nucleic Acid Tests: Comparison with Culture and Enzyme Immunoassay of Genital Swab Specimens," J. Clin Micorbiol., Dec. 1997, 35(12):3355-3357.
Skeggs, "An automatic method for colorimetric analysis," Am. J. Clin. Pathol., 1957, 28:311-322, American Society of Clinical Pathologists, Chicago, USA.
Smith et al., "Abbott AxSYM random and continuous access immunoassay system for improved workflow in the clinical laboratory," Clin. Chem., 1993, 39(10):2063-2069, American Association for Clinical Chemistry, Washington D. C., USA.
Smith et al., "Detection of *Mycobacterium tuberculosis* Directly from Sputum by Using a Prototype Automated Q-Beta Replicase Assay," J. Clin. Microbiol., 1997, 35(6):1477-1483, American Society for Microbiology, Washington, D.C., USA.
Smith et al., "Performance of an Automated Q-Beta Replicase Amplification Assay for *Mycobacterium tuberculosis* in a Clinical Trial," J. Clin. Microbiol., 1997, 35(6):1484-1491, Am. Society for Microbiology, USA.
Stanley et al., "A Survey of More Than 90 Commercially Available Luminometers and Imaging Devices for Low-Light Measurements of Chemiluminescence and Bioluminescence, Including Instruments for Manual, Automatic and Specialized Operation, for HPLC, LC, GLC and Microtitre Plates. Part 2: Photographs," J. Biolumin. Chemilumin., 1992, 7:157-169, John Wiley & Sons, Ltd., Chichester, Sussex, England.
Stanley, "Commercially Available Luminometers and Imaging Devices for Low-Light Level Measurements and Kits and Reagents Utilizing Bioluminescence or Chemiluminescence: Survey Update 3," J. Biolumin. Chemilumin., 1994, 9:123-125, John Wiley & Sons, Ltd., UK.
Stone et al., "Detection of rRNA from four respiratory pathogens using an automated Qβ replicase assay," Mol. Cell. Probes, 1996, 10:359-370, Academic Press Limited, San Diego, California, USA.
Suryanarayana et al., "Plasma SIV RNA Viral Load Determination by Real-Time Quantification of Product Generation in Reverse Transcriptase-Polymerase Chain Reaction," AIDS Res. Hum. Retroviruses, 1998, 14(2):183-189, Mary Ann Liebert, Inc., USA.
Sutton et al., "Hands Free Polymerase Chain Reaction," International Symposium on Laboratory Automation and Robotics, Oct. 17-20, 1993, p. 326-336, Boston, USA.
Sutton et al., "PCR Has Outgrown Appropriate Automated Instrumentation But Help is on the Way," Today's Chemist at Work, 1995, p. 42-48, American Chemical Society, Washington, D.C., USA.
TAOS Inc. "TCS230 Programmable Color to Light-to-Frequency Converter," www.http?pdfl.alldatasheet.com/datasheet-pdf/view/96470/ETC/TCS230.html; Jan. 31, 2003, pp. 1-8.
Techne PHC-3 Thermal Cycler—Techni, Jun. 2009, Pegasus Scientific Inc., USA.
Tjian, "Purification and comparative properties of the delta and sigma subunits of RNA polymerase from *Bacillus subtilis*" Eur. J. Biochem., 1977, 74:149, Blackwell Science Ltd. on behalf of the Federation of European Biochemical Societies, UK.
Tyagi et al., "Extremely sensitive, background-free gene detection using binary proves and QB Replicase," Biochemistry, 1996, 93:5395-5400, Proc. Natl. Acad. Sci. USA, Washington D.C., USA.
Tyagi et al., "Molecular Beacons: Probes that Fluoresce upon Hybridization," Nature Biotechnology, 1996, 14:303-308, Nature Publishing Company, New York, USA.
Uckun et al., "Clinical Significance of MLL-AF4 Fusion Transcript Expression in the Absence of a Cytogenetically Detectable t(4;11)(q21;q23) Chromosomal Translocation," Blood, 1998, 92(3):810-821, American Society of Hematology, Washington D.C., USA.

Van Gemen, Accuract B. at al.; "The One-tube Quantitative HIV-1 RNA NASBA: Precision, and Application,"; 1995; PCR Methods Appl.; vol. 4; pp. 177-184.
Victor et al., "Laboratory Experience and Guidelines for Avoiding False Positive Polymerase Chain Reaction Results," Eur. J. Clin. Chem. Clin. Biochem., 1993, 31(8):531-535, Walter de Gruyter & Co., Berlin, Germany.
Voss et al., "Direct genomic fluorescent on-line sequencing and analysis using in vitro amplification of DNA," Nucl. Acids Res., 1989, 17(7):2517-2527, IRL Press, USA.
Walker et al., "Detection of *Mycobacterium tuberculosis* DNA with thermophilic strand displacement amplification and fluorescence polarization," Clin. Chem., 1996, 42(10):1604-1608, American Association for Clinical Chemistry, Washington D.C., USA.
Walker et al., "Strand displacement amplification (SDA) and transient-state fluorescence polarization detection of *Mycobacterium tuberculosis* DNA," Clin. Chem., 1996, 42(1):9-13, American Association for Clinical Chemistry, Washington D.C., USA.
Walter et al., "Fluorescence correlation analysis of probe diffusion simplifies quantitative pathogen detection by PCR," Proc. Natl. Acad. Sci. USA, 1996, 93:12805-12810, National Academy of Sciences, Washington D.C., USA.
Whelan et al., "The Role of Nucleic Acid Amplification and Detection in the Clinical Microbiology Laboratory," Annu. Rev. Microbiol., 1996, 50:349-373, Annual Reviews, Palo Alto, USA.
Wilke et al., "Automation of Polymerase Chain Reaction Tests Reduction of Human Errors Leading to Contamination," Diagn. Microbiol. Infect. Dis., 1995, 21:181-185, Elsevier Sciences, New York City, USA.
Wilke et al., "Automation of Polymerase Chain Reaction Tests to Achieve Acceptable Contamination Rates," Clin. Chem., 1995, 41(4):622-623, American Association for Clinical Chemistry, Washington, D.C., USA.
Wittwer et al., "The LightCycler: a microvolume multisample fluorimeter with rapid temperature control," BioTechniques, 1997, 22:176-181, Informa Healthcare USA, Inc., London, United Kingdom.
Yourno et al., "A method for nested PCR with single closed reaction tubes," PCR Methods Appl., 1992, 2(1):60-65, Cold Spring Harbor Laboratory Press, Cold Spring Harbor, New York, USA.
Genprobe; "Test Procedure Guide. Amplified *Mycobacterium tuberculosis* Direct (MTD) Test,"; 2000, 1 page.
International Search Report and Written Opinion mailed on Nov. 6, 2013 for PCT Patent Application No. PCT/US2012/063918, 22 pages.
ABI Product Catalogue, 1993-1994, "DNA Sequencing Reagents," p. 146, Applied Biosystems, USA.
Anonymous, "GeneAmp optical reaction plate," Nature, 1998, 391(8):210, Nature Publishing Group, USA.
Asper et al., "Laboratory Mechanization and Automation," in Laboratory Organization Automation, 1991, pp. 271-275, Walter deGruyter, USA.
Bieche et al., "Novel Approach to Quantitative Polymerase Chain Reaction Using Real-Time Detection: Application to the Detection of Gene Amplification in Breast Cancer," Int. J. Cancer, 1998, 78:661-666, Wiley-Liss, Inc., USA.
Billyard, et al., "Early detection of HIV-1 RNA from sero-conversion panels using Gen-Probe's transcription-mediated amplification," The San Diego Conference Nucleic Acid Technology: The Cutting Edge of Discovery, Nov. 6-8, 1997, Clin. Chem., 1997, 43(11):2221, Am. Assoc. For Clin. Chem., USA.
Burg et al., "Real-time fluorescence detection of RNA amplified by Q beta replicase," Anal. Biochem., 1995, 230(2):263-272, Academic Press, Orlando, Florida, USA.
Chemistry Guide, "ABI Prism DNA Sequencing," 1995, pp. 1-3-1-6, The Perkin-Elmer Corporation, USA.
Civitello et al., "A simple protocol for the automation of DNA cycle sequencing reactions and polymerase chain reactions," DNA Sequence—J. DNA Sequencing and Mapping, 1992, 3:17-23, Harwood Academic Publishers GmbH, UK.
Dangler, ed., Nucleic Acid Analysis: Principles and BioApplications, 1996, pp. 1-3, 19, 68-75, 106-109, 116, 117, 144, 145, 157, 162 & 163, Wiley-Liss, Inc., USA.

(56) References Cited

OTHER PUBLICATIONS

Educational Guide, "New Directions in Molecular Diagnostic Testing," pp. 1-12, Rev. A, 2000, Gen-Probe Incorporated, San Diego, USA.
Felder, "Automation of Preanalytical Processing and Mobile Robotics," in Handbook of Clinical Automation, Robotics, and Optimization, 1996, pp. 252-256, John Wiley & Sons, Inc., USA.
Hawkins et al., "Thermal Cycle DNA Sequence Setup Using a Modified Lab Workstation," LRA, 1995, 7:117-122, VCH Publishers, New York City, USA.
Higuchi et al., "Kinetic PCR Analysis: Real-time Monitoring of DNA Amplification Reactions," Bio/Technology, 1993, 11(9):1026-30, Nature Publishing Group, New York, USA.
Hill et al., "The Polymerase Chain Reaction in Molecular and Microbiology," Biotechnol. Genet. Eng. Rev., 1992, 10:343-377, Taylor & Francis, UK.
Holmberg et al., "Automatic Preparation of DNA Templates for Sequencing on the ABI Catalyst Robotic Workstation," Automated DNA Sequencing and Analysis, 1994, Academic Press Inc., San Diego, USA.
Hunkapiller, "Advances in DNA sequencing technology," Curr. Opin. Genet. Dev., 1991, 1:88-92, Elsevier, UK.
Jakobsen et al., "Direct mRNA Isolation Using Magnetic Oligo (dT) Beads: A Protocol for All Types of Cell Cultures, Animal and Plant Tissues," in Advances in Biomagnetic Separation, 1994, pp. 61-71, Eaton Publishing, USA.
Kasper, "Automated Instrumentation (Generic)," in Clinical Laboratory Instrumentation and Automation: Principles, Applications, and Selection, 1994, pp. 184-205, W.B. Saunders Company USA.
Kaufman et al., "Direct Sequencing by PCR," in Handbook of Molecular and Cellular Methods in Biology and Medicine, 1995, pp. 233-235, CRC Press, USA.
Krieg, ed., "Quantitation of RNA Transcripts Using RT-PCR," in A Laboratory Guide to RNA: Isolation, Analysis, and Synthesis, 1996, pp. 176-190, John Wiley & Sons, Inc., USA.
Little et al., "Recent Advances in Robotic Automation of Microplate Assays," Lab. Info. Mgmt., 1994, 26:89-99, Elsevier Science, Amsterdam, Netherlands.
Lundeberg et al., "Solid-Phase Technology: Magnetic Beads to Improve Nucleic Acid Detection and Analysis," Biotechnol. Annu. Rev., 1995, 1:373-401, Elsevier Science, Amsterdam, Netherlands.
Mahan et al., "An Automated System for Infectious Disease Diagnosis with Q-Beta Replicase Amplification," in New Horizons in Gene Amplification Technologies: Proceedings of a CHI Meeting, 1994, Cambridge, USA, 25 pages.
McDonough et al., High Throughput Assay for the Simultaneous or Separate Detection of Human Immunodeficiency Virus (HIV) and Hepatitis Type C Virus (HCV), Infusionsther. Transfusionsmed, 1998, 25:164-169, Karger GmbH, Germany.
Mertes et al., Automatische genetische Analytik, 1997, forward and pp. 68, 69, 73 & 74, Wiley-VCH, Germany; German Language Reference.
Mizutani et al., "Magnetic Separation in Molecular Studies of Human Leukemia,"in Advances in Biomagnetic Separation, 1994, p. 127-133, Eaton Publishing, USA.
Olsvik et al., "Magnetic Separation in Laboratory Diagnosis of Infectious Diseases," in Advances in Biomagnetic Separation, 1994, pp. 149-158, Eaton Publishing, USA.

Olympus Corporation, "Olympus News Release: Automated Chemistry Analyser AU1000," 1997, http://www.olympus-global.com/en/news/1997a/nr970421au1000e.jsp, downloaded Jun. 17, 2013, USA, 3 pages.
Overbergh et al., "Quantification of Murine Cytokine mRNAs Using Real Time Quantitative Reverse Transcriptase PCR," Cytokine, 1999, 11(4):305-312, Academic Press, USA.
Petrik et al., "High throughput PCR detection of HCV based on semiautomated multisample RNA capture," J. Virol. Methods, 1997, 64:147-159, Elsevier/NorthHolland Biomedical Press, Amsterdam, Netherlands.
Piatek et al., "Molecular beacon sequence analysis for detecting drug resistance in *Mycobacterium tuberculosis*," Nature Biotechnology, 1998, 16:359-363, Nature America Publishing, New York, USA.
Shah et al., "Novel, Ultrasensitive, Q-Beta Replicase-Amplified Hybridization Assay for Detection of *Chlamydia trachomatis*," J. Clin. Microbiol., 1994, 32(11):2718-2724, American Society for Microbiology, USA.
Slatko, "Thermal Cycle Dideoxy DNA Sequencing," in Protocols for Gene Analysis (Methods in Molecular Biology), 1994, vol. 31, pp. 35-45, Humana Press Inc., USA.
Sloan et al., "Screening Yeast Artificial Chromosome Libraries with Robot-Aided Automation," GATA, 1993, 10(6):128-143, Elsevier Science Publishing Co., Inc., USA.
Truchaud et al., "Liquid-Phase Reactions Started by Rehydrating Lyophilized Reagents in a Centrifugal Analyzer," Clin. Chem., 1985, 31(9):1506-1508, Am. Assoc. For Clin. Chem., USA.
Tyagi et al., "Multicolor molecular beacons for allele discrimination," Nat. Biotechnol., 1998, 16:49-53, Nature Publishing Group, USA.
Vonderschmitt, ed., "Robots in the Clinical Laboratory," in Laboratory Automation Organization, 1991, pp. 576-577, Walter deGruyter, USA.
Ward, ed., "Improving Laboratory Efficiency Through Workflow Analysis", in Clinical Laboratory Instrumentation and Automation: Principles, Applications, and Selection, 1994, pp. 453 & 457, W.B. Saunders Company, USA.
Webster's New World Dictionary, Third college Edition, 1988: Definition of Incubate, Incubator.
Yohda et al., "Development of a Novel Laboratory Automation System for Molecular Biology," Kaguku-Koguku Symposium, 1998, p. 17-20.
International Search Report and Written Opinion mailed on Feb. 15, 2013 for PCT Application No. PCT/US2012/063923, 12 pages.
Astle, "Standards in Robotics and Instrucmentation," Society Updates, Working Group Updates, and Conference Highlights, J. Biomol. Screen., 1996, 1(4):161172, Sage Publications, USA.
Amplification Technical Bulletin, "Comparison of TMA with PCR and LCR Amplification Methods," undated, Gen-Probe Incorporated, San Diego, USA, 1 page.
Brochure, "Amplified Mycobacteria Direct Tests," undated, Gen-Probe Incorporated, San Diego, USA, 6 pages.
Jaklevic, "Automation of High-Throughput PCR Assays," Laboratory Robotics and Automation, 1996; 8(5):277-286, John Wiley & Sons Inc., USA.
International Search Report and Written Opinion mailed on Aug. 9, 2012 for PCT Patent Application No. PCT/US2012/037585, 10 pages.

\* cited by examiner

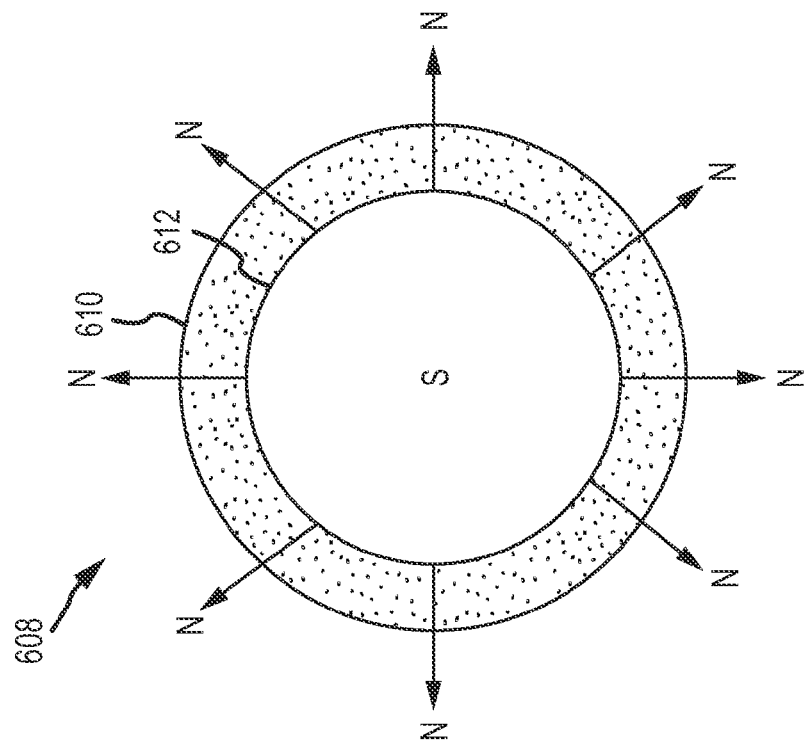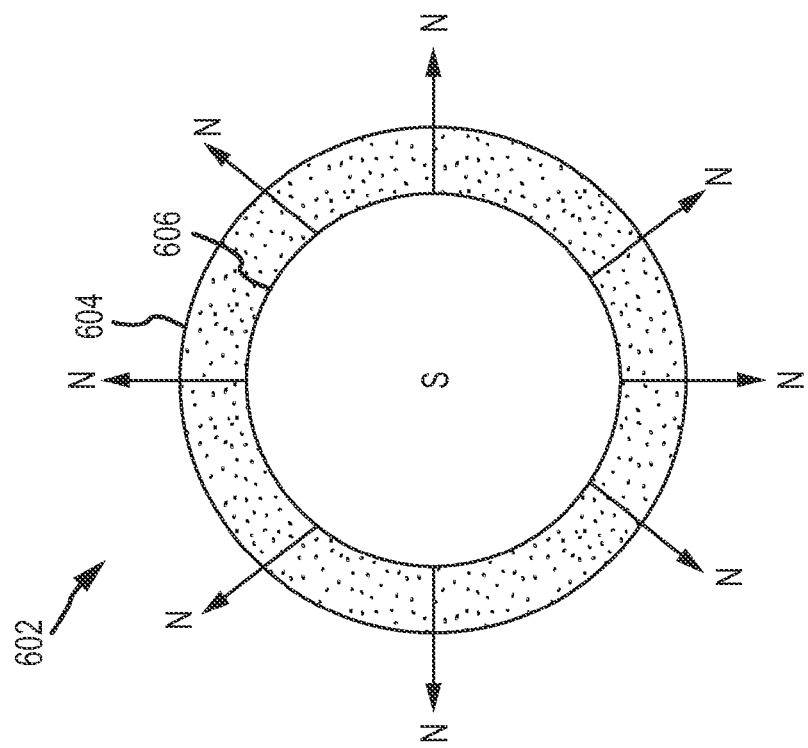
FIG. 6

MAGNETIC DAMPING FOR SPECIMEN TRANSPORT SYSTEM

CROSS-REFERENCES TO RELATED APPLICATIONS

This application claims priority to U.S. Provisional Patent Application No. 61/556,667, filed Nov. 7, 2011 and entitled "Analytical System and Method for Processing Samples," herein incorporated by reference in its entirety for all purposes. This application also claims priority to U.S. Provisional Patent Application No. 61/616,994, filed Mar. 28, 2012 and entitled "Analytical System and Method for Processing Samples," herein incorporated by reference in its entirety for all purposes. This application further claims priority to U.S. Provisional Patent Application No. 61/680,066, filed Aug. 6, 2012 and entitled "Analytical System and Method for Processing Samples," herein incorporated by reference in its entirety for all purposes.

BACKGROUND

A specimen transport system may be used to convey specimens within a laboratory analysis system. Specimens may be samples of blood or other bodily fluids on which laboratory analysis is to be performed. Preparation of a sample for analysis may require transporting the sample to various stations for aliquotting, centrifuging, or other processes. The sample may then be transported to a location where analysis to be performed and to an output station for storage or disposal. Various transportation systems may be used to transport samples between stations of a laboratory analysis system.

A conveyor transport system may use a conveyor belt or conveyor track to transport sample tubes between stations. Typically, a sample tube is inserted into a sample carrier that holds the specimen in a fixed upright position for transport by the conveyor system. Routing mechanisms such as diverting arms may be used to divert the sample carriers from one conveyor to another (e.g., the main conveyor to an auxiliary conveyor).

Conveyor systems may be operated at low speeds to avoid the potential occurrence of sample carrier impacts. Impacts can occur between sample carriers when a first sample carrier encounters an obstacle and the sample carriers following the first sample carrier collide as they form a queue behind the obstacle. An impact may also occur when a sample carrier encounters a diverting arm on a track. These impacts may cause the contents of a sample tube to splash out from a sample carrier. Impacts may also affect sample quality by causing fluid layers separated by centrifugation to remix.

Embodiments of the invention solve these and other problems.

BRIEF SUMMARY

Embodiments of the technology relate to systems and methods for efficiently processing samples collected for laboratory analysis. More specifically, a sample carrier transport system having magnetic damping components is described.

One embodiment is directed to a specimen transport system. A first sample carrier magnet is coupled to a first sample carrier configured to transport at least one specimen container and a second sample carrier magnet is coupled to a second sample carrier configured to transport at least one specimen container. A conveyance device transports a plurality of sample containers. The first sample carrier magnet is configured to repel the second sample carrier magnet such that no contact occurs between the first sample carrier and the second sample carrier when the first sample carrier is transported toward the second sample carrier.

Another embodiment is directed to a specimen transport system having a sample carrier magnet coupled to a sample carrier and a diverting arm magnet coupled to a diverting arm. A conveyance device transports sample carriers such that the sample carrier is transported toward the diverting arm. The diverting arm magnet is configured to repel the sample carrier magnet such that no contact occurs between the sample carrier and the diverting arm when the sample carrier is transported toward the diverting arm.

A further embodiment is directed to a method for transporting specimens. A conveying device transports a plurality of sample carriers. A first sample carrier magnet of a first sample carrier repels a second sample carrier magnet of a second sample carrier such that no contact occurs between the first sample carrier and the second sample carrier when the first sample carrier is transported toward the second sample carrier.

An additional embodiment is directed to a sample carrier assembly. The sample carrier assembly includes a sample carrier. The sample carrier is configured to transport at least one specimen container. The sample carrier assembly also includes a sample carrier magnet that is coupled to the sample carrier.

These and other embodiments of the technology are described in further detail below.

BRIEF DESCRIPTION OF THE DRAWINGS

A further understanding of the nature and advantages of the different embodiments may be realized by reference to the following drawings.

FIG. 6 is a diagram illustrating the magnetization of two sample carrier ring magnets.

DETAILED DESCRIPTION

Embodiments of the present technology relate to systems and methods of magnetic damping for sample carriers used in a specimen transport system for medical laboratory analysis.

A laboratory automation system may have one or more means of transporting specimen containers from one location within the system to another location. For example, a conveyor system having a conveyor belt or track may be used to move specimen containers.

Specimen containers may be any vessel used to contain a sample of a bodily fluid, such as blood, or any other fluid requiring laboratory analysis. A specimen container may be a sample tube. In some embodiments, a sample is centrifuged prior to analysis. For example, blood may be separated into layers of constituent materials and other materials (e.g., plasma, red blood cells, buffy coat, gel) by centrifugation.

One or more specimen containers may be placed in a sample carrier for transportation of the specimens between locations via a transport system. In some embodiments, sample carriers have resilient elements, such as spring loaded jaws, to accommodate sample tubes having varying dimensions. Once the specimen container is inserted into the sample carrier, the sample carrier preferably holds the specimen container in a fixed position relative to the sample carrier. The specimen container can be removed from the sample carrier when the sample carrier reaches a designated destination for the specimen container. The sample carrier may include a motor that allows the sample carrier to move independently. Exemplary embodiments of independently movable sample carriers are described in PCT Patent Application No. PCT/US2012/037585, filed May 11, 2012 and entitled "System and Method Including Laboratory Product Transport Element," herein incorporated by reference in its entirety for all purposes.

Introducing magnets in the sample carriers, such that a magnet of a first sample carrier repels the magnet of an adjacent sample carrier, can prevent the adverse effects that may occur when sample carriers collide with one another. As a result, sample carriers may travel at increased speeds with little to no adverse impact on sample quality.

In some embodiments, one or more magnetic elements may be coupled to a directional gate. A directional gate may be used to move a sample carrier from one track to another track. Existing directional gates can cause a sample carrier to slow down due to friction between the sample carrier and the gate. When a magnet is coupled to a directional gate, the magnet can repel a sample carrier magnet on a sample carrier such that there is no contact between the sample carrier and the directional gate. In this way, the speed at which the sample carriers are able to traverse the directional gates may be increased.

Magnets used in sample carriers and directional gates may be made of any material or device that produces a magnetic field, such as metallic magnets, ceramic magnets, or electromagnets.

Figure 1:
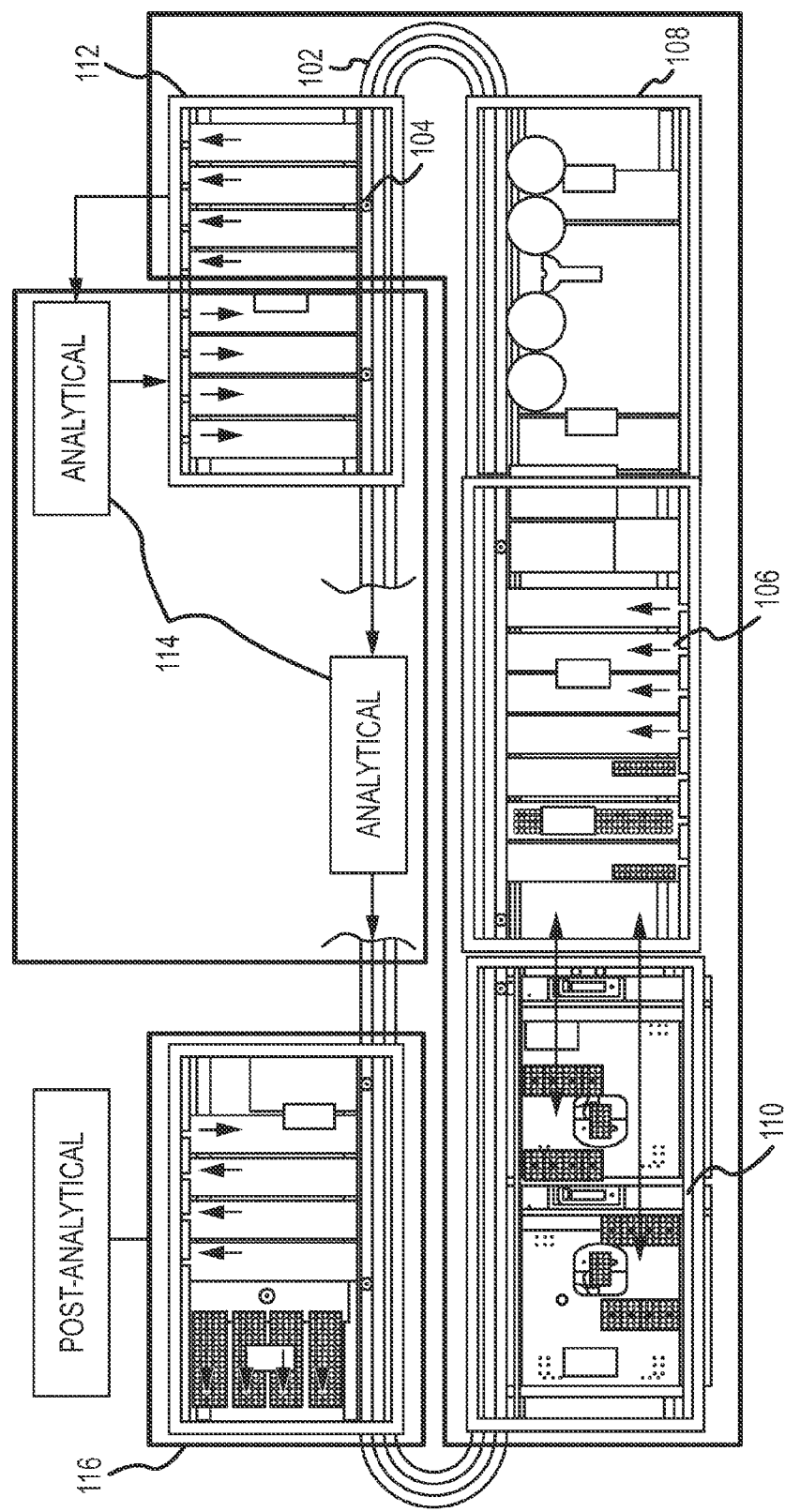
FIG. 1 shows an illustrative embodiment of conveyor system used to transport sample carriers in a laboratory automation system for processing patient samples.

FIG. 1 shows an illustrative embodiment of a conveyor system used to transport sample carriers in a laboratory automation system for processing patient samples. The laboratory automation system may use a conveyor track to transport sample carriers between various areas of the laboratory automation system. For example, conveyor track 102 may be used to transport sample carriers 104 between one or more of, e.g., a specimen container input and distribution area 106, an aliquotter area 108, a centrifuge area 110, an output area 112, analytical areas 114, and a post-analytical sample processing area 116.

Directional gates may be used to guide sample carriers traveling along a conveyor system. For example, a directional gate may be a diverting arm used to divert a sample carrier from one track to an adjacent track. In some embodiments, a directional gate may be operated under the control of one or more processors. For example, a controller of the conveyor transport system may be communicatively coupled to a main controller for the laboratory automation system. The conveyor transport system controller may operate the directional gate in response to commands received from the main controller in order to divert sample carriers to a desired conveyor track or sample carrier destination. FIGS. 2(a)-2(d) depict illustrative examples of diverter and merger functions that can be used in a conveyor transport system.

Figure 2:
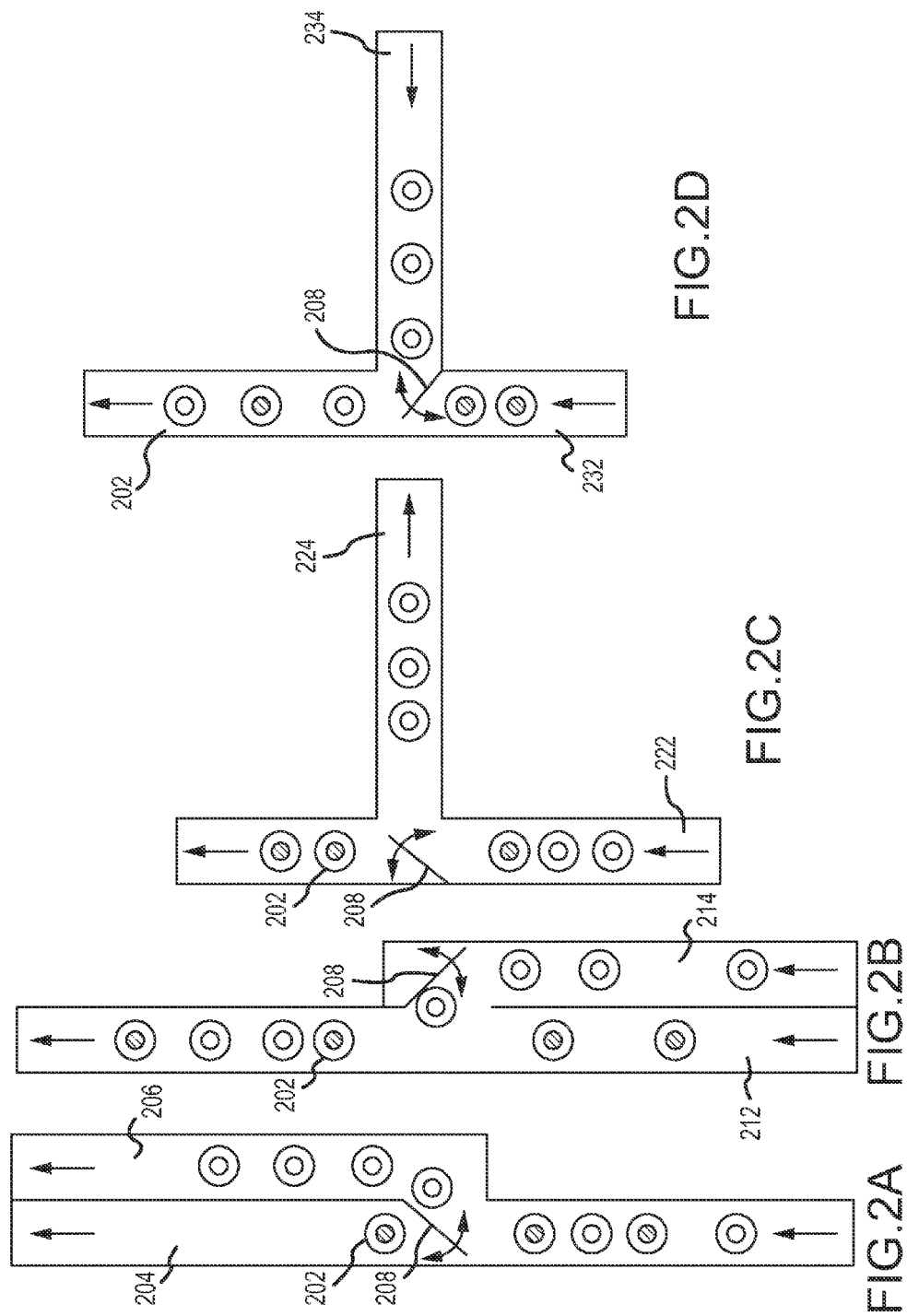
FIGS. 2(*a*)-(*d*) depict illustrative examples of diverter and merger functions that can be used in a conveyor transport system.

FIG. 2(a) shows a conveyor transport system capable of diverting sample carriers 202 from one track 204 to an adjacent parallel track 206. The sample tubes may be diverted when the conveyor transport system controller instructs a diverting arm 208 to move to a position such that the sample tubes can be diverted to a parallel conveyance line.

As shown in FIG. 2(b), the conveyor transport system may also merge two conveyance tracks that are parallel to each other. Sample carriers 202 from first conveyor track 212 can be merged with sample tubes coming down the second conveyor track 214. In some embodiments, a controller such as the conveyor transport system controller can coordinate the timing for entry of sample carriers 202 onto the conveyor tracks 212, 214 and/or operation of the diverter arm 208 such that sample carriers do not run into one another and/or become jammed on the line.

The conveyor transport system is also capable of diverting sample carriers travelling from a first conveyance line 222 to a second conveyance line 224 that is perpendicular to the first conveyance line, as shown in FIG. 2(c). Sample carriers traveling along conveyor 222 can be diverted 90° to conveyor 224 by diverter arm 208. It will be recognized that conveyor tracks 222 and 224 may intersect at angles other than 90° angles.

As shown in FIG. 2(d), the conveyor transport system may also be capable of merging sample tubes onto a first conveyance line 232 from a perpendicular second conveyance line 234. First conveyor track 232 can be perpendicular to second conveyor track 234. It will be recognized that the conveyor tracks may intersect at angles other than 90° angles. Sample carriers traveling along second conveyor 234 can be merged onto first conveyor 232. In some embodiments, a controller such as the conveyor transport system controller can coordinate the timing for entry of sample carriers 202 onto the conveyor tracks 232, 234 and/or operation of the diverter arm 208 such that sample carriers do not run into one another and/or become jammed on the line.

Figure 3:
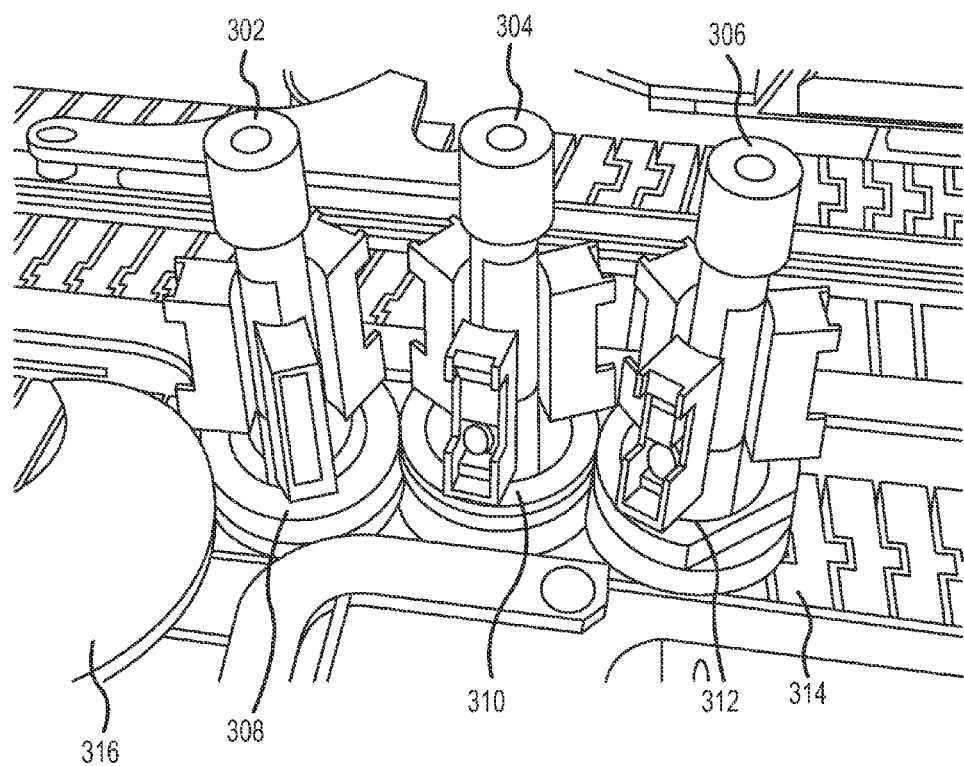
FIG. 3 shows a prior art conveyor transport system.

FIG. 3 shows a prior art conveyor transport system in which specimen containers 302, 304, and 306 are being transported by sample carriers 308, 310 and 312, respectively, along conveyor track 314. In the illustrative prior art system, sample carrier 308 has traveled along conveyor track 314 until the sample carrier encountered obstacle 316. Sample carrier 310, which was traveling behind sample carrier 308, has collided with sample carrier 308 after sample carrier 308 was stopped by obstacle 316. Sample carrier 312 has likewise collided with sample carrier 310. Such collisions can cause sample material to splash out of the sample carrier. If the sample material has been separated into layers (e.g., blood separated into its component parts by centrifugation), the collisions can disturb the layers, causing the separated sample material to recombine. The prior art conveyance system must be run at a sufficiently slow rate to prevent spillage and disturbance of the samples.

In various embodiments of an improved specimen transport system that utilizes magnetic damping, magnets are coupled to sample carriers. For example, a ring magnet may be integrated into or otherwise affixed to a sample carrier. In some embodiments, the ring magnet is coupled to the sample carrier such that the ring magnet encircles the sample carrier. When a sample carrier having a ring magnet encounters another sample carrier having a ring magnet, the respective ring magnets repel one other such that the respective sample carriers decelerate. In this way, collisions can be prevented or dampened.

Figure 4:
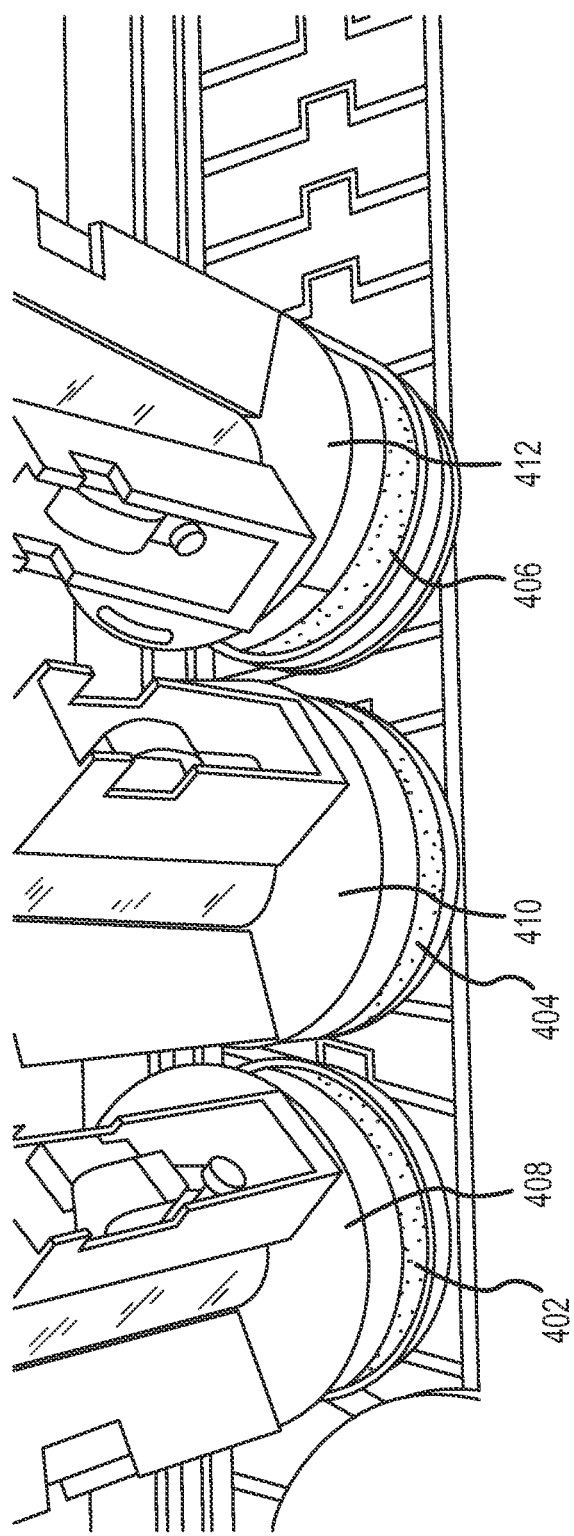
FIG. 4 shows illustrative sample carriers of a specimen transport system with magnetic damping components, according to an embodiment.

FIG. 4 shows illustrative sample carriers of a specimen transport system with magnetic damping components. First sample carrier magnet 402, second sample carrier magnet 404, and third sample carrier magnet 406, are coupled to first sample carrier 408, second sample carrier 410, and third sample carrier 412, respectively. A specimen container (such as the specimen containers 302-306 described with reference to FIG. 3) can be inserted in each sample carrier.

Sample carrier magnets 402-406 may be ring-shaped magnets. In some embodiments, the ring magnet may be coupled to the base of the sample carrier (e.g., below the portion of the specimen container that receives the specimen container). The ring magnet may be mounted such that the exterior of the ring magnet is flush with the external surface of the sample carrier. The ring magnet may be radially magnetized such that a first pole of the magnet is the outer surface of the ring and a second pole of the magnet is the inner surface of the ring. Preferably, the pole of the outer surface of each sample carrier ring magnet is matched such that the sample carrier magnets repel one another. Thus, if the outer surface of the first sample carrier magnet is a north pole, the outer surface of the second sample carrier magnet and the third sample carrier magnet are also magnetized such that the outer surface of the ring magnets is a north pole.

In FIG. 4, first sample carrier magnet 402 repels second sample carrier magnet 404, causing a space to be maintained between sample carrier 408 and 410. Similarly, second sample carrier magnet 404 repels third sample carrier magnet 406, causing a space to be maintained between sample carriers 410 and 412. In this manner, collisions between adjacent sample carriers are prevented by the repelling effect of the respective magnetic fields of the magnets coupled to the sample carriers.

In some embodiments, a diverting arm magnet is coupled to a diverting arm such that the diverting arm magnet repels the sample carrier magnet of any sample carrier that approaches the diverting arm.

Figure 5:
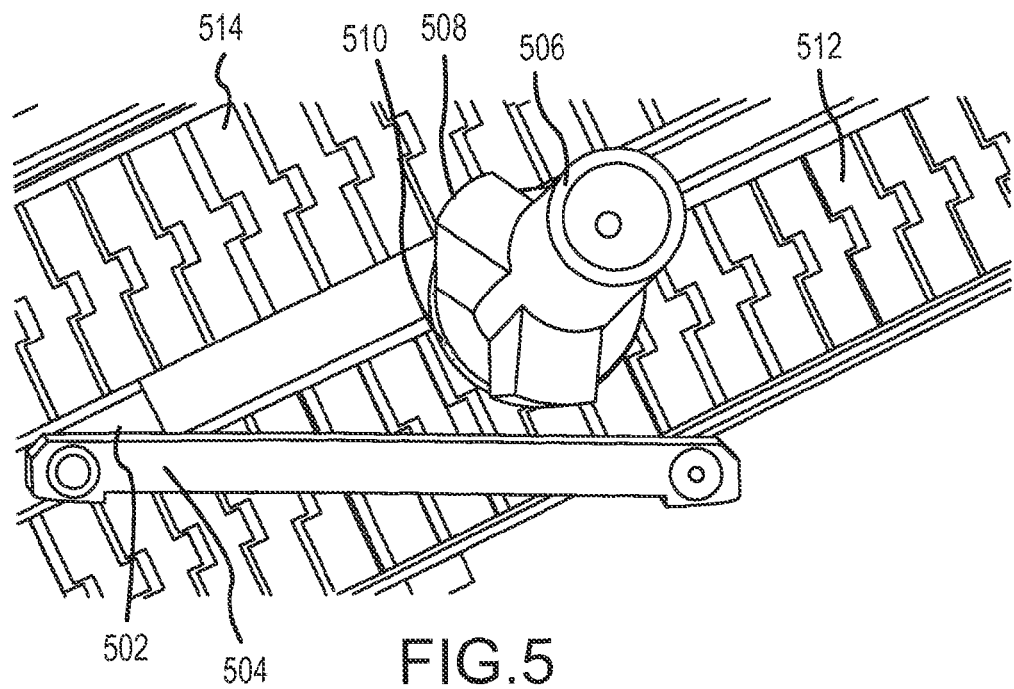
FIG. 5 shows a top view of an illustrative diverting arm with a diverting arm magnet.

FIG. 5 is a top view of an illustrative diverting arm with a diverting arm magnet. One or more diverting arm magnets 502 may be coupled to diverting arm 504. In some embodiments, diverting arm 504 is fabricated from a material that is magnetized such that it is not necessary to couple a separate magnetic component 502 to diverting arm 504. Specimen container 506 is inserted into sample carrier 508 having sample carrier magnet 510. Sample carrier 508 is transported by first conveyor track 512 toward diverting arm 504.

Diverting arm magnet 502 may be magnetized such that the pole of diverting arm magnet 502 that faces sample carrier 508 is the same as the pole of the exterior surface of sample carrier magnet 510. For example, if diverting arm magnet 502 has a north pole facing sample carrier magnet 510, the exterior surface of sample carrier magnet 510 may be magnetized such that the outer surface of the ring magnet is a north pole. In this manner, when sample carrier 508 approaches diverting arm 504, diverting arm magnet 502 repels sample carrier magnet 510, such that an impact between diverting arm 504 and sample carrier 508 is reduced or avoided. When diverting arm 504 is in a first position such that diverting arm 504 extends across first conveyor track 512, sample container 508 is urged by first conveyor track 512 and diverting arm 504 onto second conveyor track 514. When diverting arm 504 is in a second position (not shown) such that diverting arm 504 does not extend across first conveyor track 512, sample container 508 will continue along first conveyor track 512 undiverted.

FIG. 6 is a diagram of a first ring magnet associated with a first sample carrier (not shown) and a second ring magnet associated with a second sample carrier (not shown). First ring magnet 602 may be radially magnetized such that a first pole of the magnet is at outer surface 604 of the ring and a second pole of the magnet is at the inner surface 606 of the ring. Second ring magnet 608 may be radially magnetized such that a first pole of the magnet is at outer surface 610 of the ring and a second pole of the magnet is at the inner surface 612 of the ring. Because first ring magnet and second ring magnet have the same pole at the outer surface of the rings (such as the north pole, as shown in FIG. 6), the first ring magnet repels the second ring magnet. So long as the force driving the first sample carrier toward the second sample carrier (or vice versa) is less than the force of the magnetic field, the first sample carrier is prevented from coming into contact with the second sample carrier.

The magnetic field of the first ring magnet, the second ring magnet, and/or the diverting arm may be in the range of 150-300 Gauss as measured at a distance of 10 millimeters from the exterior surface of the magnet, such as 200-260 Gauss as measured at a distance of 10 millimeters from the exterior surface of the magnet, e.g., 242 Gauss as measured at a distance of 10 millimeters from the exterior surface of the magnet.

Figure 7:
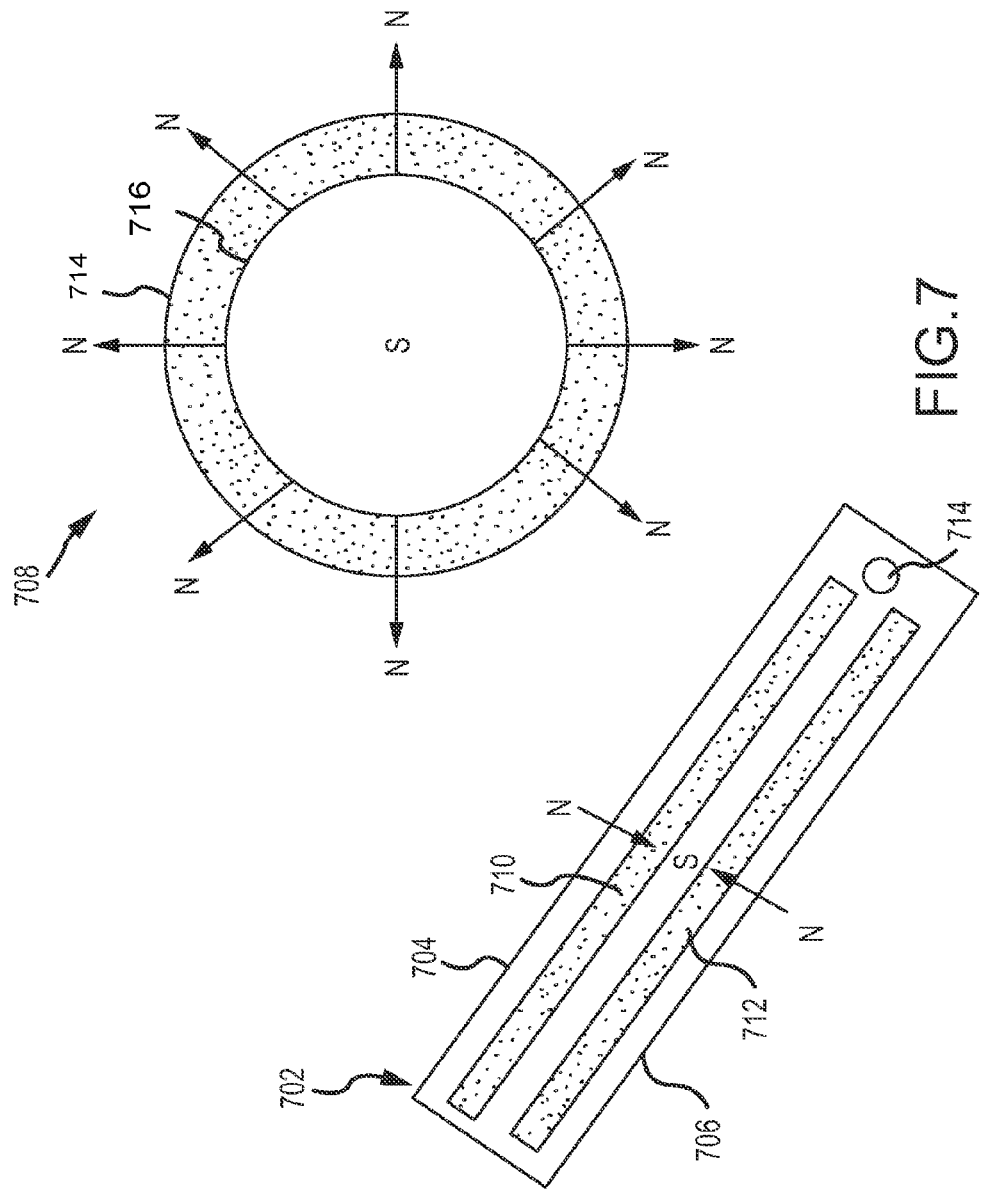
FIG. 7 is a diagram illustrating the magnetization of a sample carrier ring magnet and a diverting arm.

FIG. 7 is a diagram of one or more diverting arm magnets associated with a diverting arm and a ring magnet associated with a sample carrier. Diverting arm 702 may be pivotally coupled to the conveyor system such that it pivots about pivot point 714. Diverting arm 702 may include one or more magnets, such as first diverting arm magnet 710 and second diverting arm magnet 712. Advantageously, in a diverting arm with two magnets, first diverting arm magnet 710 can repel sample carrier magnets of sample carriers approaching the first face 704 of the diverting arm and second diverting arm magnet 712 can repel sample carrier magnets of sample carriers approaching the second face 706 of the diverting arm. For example, in FIG. 2D, sample carriers transported by conveyor track 232 may approach a first face of diverting arm 208 and sample carriers transported by conveyor track 234 may approach a second face of diverting arm 208.

First diverting arm magnet 710 and second diverting arm magnet 712 can be coupled to diverting arm 702 by a variety of means known in the art. For example, diverting arm magnets 710, 712 can be coupled to the surface diverting arm 702 with adhesive. In some embodiments, diverting arm magnet 710 and second diverting arm magnet 712 can be embedded within diverting arm 702. In other embodiments, diverting arm magnet 710 and second diverting arm magnet 712 can be coupled to a first face and a second face of diverting arm 702, respectively. The first face of diverting arm 702 can be a face with which sample carriers come into contact and the second face of diverting arm 702 can be opposite to the first face.

Preferably, the pole at the exterior surface of diverting arm 702 that will face the sample carrier is the same as the pole at the exterior surface of sample carrier magnet 708. For example, if first diverting arm magnet 710 has a north pole facing sample carrier magnet 708, as shown in FIG. 7, the outer surface 714 of sample carrier magnet 708 is preferably magnetized such that the outer surface 714 of the ring magnet 708 is a north pole and such that the inner surface 716 of the ring magnet 708 is a south pole. In this manner, when sample carrier 708 approaches diverting arm 702, diverting arm magnet 702 repels sample carrier magnet 708, such that friction between diverting arm 702 and sample carrier 708 is reduced or avoided.

In some embodiments, diverting arm 702 has a single magnet that may be axially magnetized such that a first pole is at a first surface 704 of diverting arm 702 that faces ring magnet 708 and a second pole is at a second surface 706 of diverting arm 702.

Because collisions between sample carriers can be prevented or avoided by incorporating magnets into the sample carriers, the sample carriers can be transported at high track speeds with a reduced risk of disturbing the sample. In some embodiments, incorporating sample carrier magnets and diverting arm magnets into a specimen transport system allows specimens to be transported at speeds of 100 mm/s to 200 mm/s, such as 130 mm/s to 170 mm/s, e.g., 150 mm/s.

Figure 8:
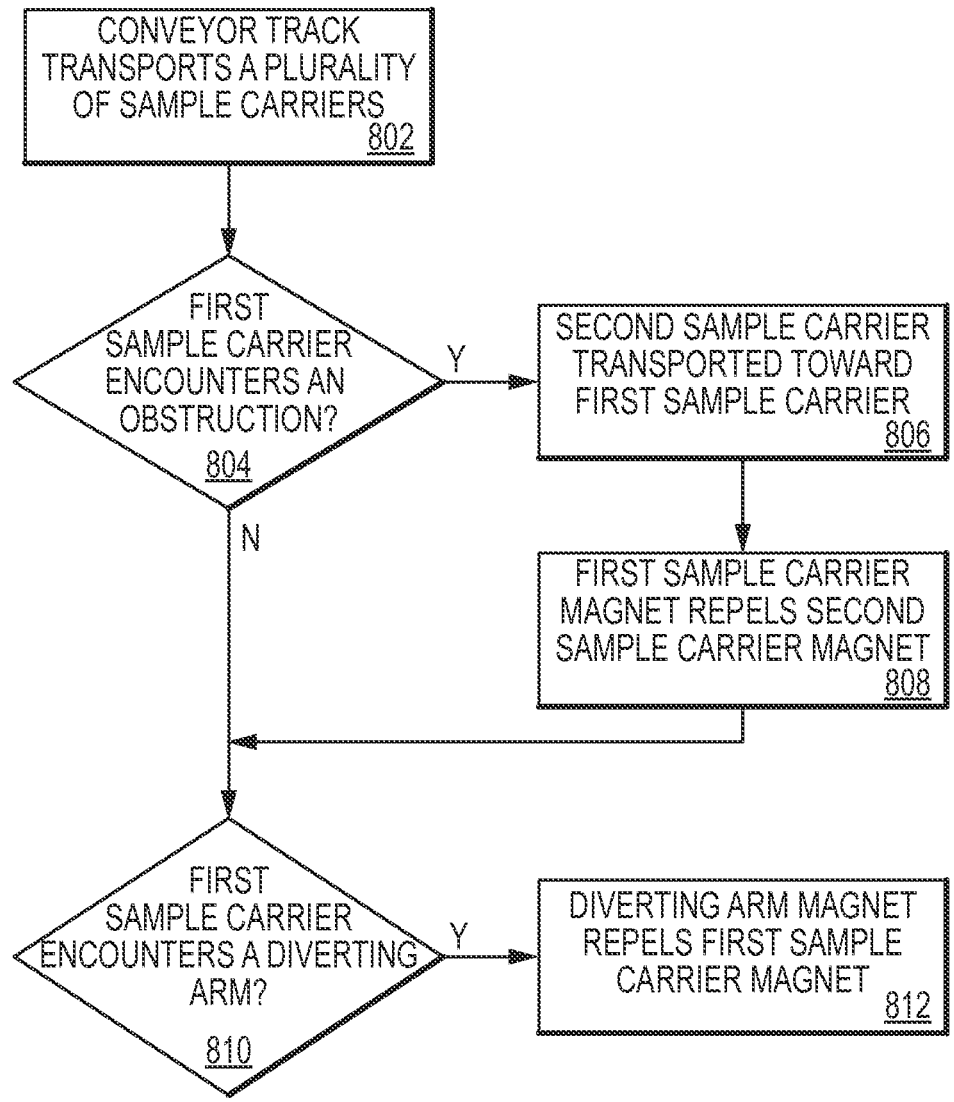
FIG. 8 is a flow chart showing an illustrative example of how magnetic damping can be used in a conveyor transport system.

FIG. 8 shows an illustrative flow diagram of magnetic damping in a conveyor transport system. At operation 802, a conveyor device such as a conveyor track transports a plurality of sample carriers. If a first sample carrier encounters an obstruction, as indicated at 804, a second sample carrier is transported toward the first sample carrier, as indicated at operation 806. The first sample carrier magnet coupled to the first sample carrier repels the second sample carrier magnet coupled to the second sample carrier such that the second sample carrier does not collide with the first sample carrier, as indicated at operation 808. If a first sample carrier encounters a diverting arm, as indicated at 810, a diverting arm magnet of the diverting arm repels a first sample carrier magnet of the first sample carrier such that the first sample carrier does not collide with the diverting arm, as indicated at operation 812.

The above description is illustrative and is not restrictive. Many variations of the technology will become apparent to those skilled in the art upon review of the disclosure. The scope of the technology should, therefore, be determined not with reference to the above description, but instead should be determined with reference to the pending claims along with their full scope or equivalents.

One or more features from any embodiment may be combined with one or more features of any other embodiment without departing from the scope of the technology.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. A specimen transport system comprising:
    a first sample carrier configured to transport at least one specimen container;
    a first sample carrier magnet coupled to the first sample carrier;
    a second sample carrier configured to transport at least one specimen container;
    a second sample carrier magnet coupled to the second sample carrier;
    wherein the first sample carrier magnet is configured to repel the second sample carrier magnet such that no contact occurs between the first sample carrier and the second sample carrier when the first sample carrier is transported toward the second sample carrier; and
    wherein the first sample carrier and the second sample carrier are adapted to be transported within the specimen transport system by a motor of the sample carrier.

2. The specimen transport system of claim 1 further comprising a diverting arm magnet coupled to a diverting arm, wherein the diverting arm magnet is configured to repel a sample carrier magnet of a sample carrier.

3. The specimen transport system of claim 2, wherein the diverting arm magnet is axially magnetized.

4. The specimen transport system of claim 1, further comprising a diverting arm, wherein the diverting arm includes:
    a first diverting arm magnet configured to repel a sample carrier magnet of a sample carrier approaching the first face of the diverting arm, and
    a second diverting arm magnet configured to repel a sample carrier magnet of a sample carrier approaching the second face of the diverting arm.

5. The specimen transport system of claim 1, wherein the sample carrier magnet is a ring magnet.

6. The specimen transport system of claim 5, wherein the ring magnet is radially magnetized.

7. The specimen transport system of claim 5, wherein the ring magnet is coupled to the sample carrier such that the exterior of the ring magnet is flush with the external surface of the sample carrier.

8. The specimen transport system of claim 1, wherein the first sample carrier is transported toward the second sample carrier at a rate of 150 millimeters per second.

9. A specimen transport system comprising:
    a sample carrier configured to transport a specimen container;
    a sample carrier magnet coupled to the sample carrier;
    a diverting arm magnet coupled to a diverting arm; and
    wherein the diverting arm magnet is configured to repel the sample carrier magnet such that no contact occurs between the sample carrier and the diverting arm when the sample carrier is transported toward the diverting arm.

10. The specimen transport system of claim 9, wherein the diverting arm magnet is axially magnetized.

11. The specimen transport system of claim 9, wherein the sample carrier magnet is a ring magnet.

12. The specimen transport system of claim 11, wherein the ring magnet is radially magnetized.

13. The specimen transport system of claim 11, wherein the ring magnet is coupled to the sample carrier such that the exterior of the ring magnet is flush with the external surface of the sample carrier.

14. The specimen transport system of claim 9, wherein the sample carrier is transported toward the diverting arm at a rate of 150 millimeters per second.

15. A method for transporting specimens, the method comprising:
    transporting, by a first motor of a first sample carrier, the first sample carrier;
    transporting, by a second motor of a second sample carrier, the second sample carrier;
    repelling, by a first sample carrier magnet of the first sample carrier, a second sample carrier magnet of the second sample carrier, such that no contact occurs between the first sample carrier and the second sample carrier when the first sample carrier is transported toward the second sample carrier.

16. The method of claim 15, the method further comprising:
    repelling, by a diverting arm magnet of a diverting arm, the first sample carrier magnet such that no contact occurs between the first sample carrier and the diverting arm when the first sample carrier is transported toward the diverting arm.

17. The method of claim 15, wherein the conveying device transports the plurality of sample carriers at a rate of 150 millimeters per second.

18. A first sample carrier configured to transport at least one specimen container, comprising:
    a first sample carrier magnet coupled to the sample carrier;
    a motor of the sample carrier for moving the sample carrier independently from at least a second sample carrier, wherein the first sample carrier magnet is configured to repel a second sample carrier magnet of the second sample carrier, such that no contact occurs between the first sample carrier and the second sample carrier when the first sample carrier is transported toward the second sample carrier.

19. The sample carrier assembly of claim 18 wherein the magnet is in the form of a ring, and encircles the sample carrier.

\* \* \* \* \*